US012078644B2

(12) United States Patent
Hosokawa et al.

(10) Patent No.: US 12,078,644 B2
(45) Date of Patent: Sep. 3, 2024

(54) ORGANIC SALT, HYDROXY-RADICAL SENSOR INCLUDING SAME, AND DETECTION MEDIUM

(71) Applicant: Panasonic Corporation, Kadoma (JP)

(72) Inventors: Teppei Hosokawa, Hyogo (JP); Norimitsu Tohnai, Osaka (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 918 days.

(21) Appl. No.: 17/253,507

(22) PCT Filed: Apr. 18, 2019

(86) PCT No.: PCT/JP2019/016712
§ 371 (c)(1),
(2) Date: Dec. 17, 2020

(87) PCT Pub. No.: WO2019/244464
PCT Pub. Date: Dec. 26, 2019

(65) Prior Publication Data
US 2021/0270853 A1    Sep. 2, 2021

(30) Foreign Application Priority Data
Jun. 22, 2018    (JP) .................. 2018-119343

(51) Int. Cl.
*G01N 33/84*    (2006.01)
*C07C 63/28*    (2006.01)
(Continued)

(52) U.S. Cl.
CPC ............. *G01N 33/84* (2013.01); *C07C 63/28* (2013.01); *C07C 211/07* (2013.01); *G01N 21/6486* (2013.01)

(58) Field of Classification Search
None
See application file for complete search history.

(56) References Cited

U.S. PATENT DOCUMENTS 2,810,696 A    10/1957  Warren et al.
2019/0376903 A1  12/2019  Kurata et al.

FOREIGN PATENT DOCUMENTS

CN    108047035    5/2018
JP    H05336997    12/1993
(Continued)

OTHER PUBLICATIONS

Machine generated English language translation of Seki (JPH0668455A, published on Mar. 11, 1994). (Year: 2023).*

(Continued)

*Primary Examiner* — Amy C Bonaparte
(74) *Attorney, Agent, or Firm* — HSML P.C.

(57) ABSTRACT

An organic salt of the present disclosure contains terephthalic acid and at least one kind of primary alkylamine. An alkyl group constituting the primary alkylamine has 6 or more and 17 or less carbon atoms. The organic salt of the present disclosure can be used to detect a hydroxy radical contained in a gas, for example. The present disclosure provides: an organic salt that makes it possible to detect a hydroxy radical more easily as well as to detect a hydroxy radical generated in a living body; and a hydroxy-radical sensor adopting the organic salt.

10 Claims, 15 Drawing Sheets

(51) Int. Cl.
*C07C 211/07* (2006.01)
*G01N 21/64* (2006.01)

(56) References Cited

FOREIGN PATENT DOCUMENTS

| JP | H05336998 | 12/1993 |
| JP | H0668455 | 3/1994 |
| JP | 2002088015 | 3/2002 |
| JP | 2002088194 | 3/2002 |
| JP | 3838902 B2 | 10/2006 |
| JP | 2012098114 | 5/2012 |
| JP | 2013205061 | 10/2013 |
| JP | 5740138 | 6/2015 |
| JP | 2018040639 | 3/2018 |
| WO | 9728687 | 8/1997 |
| WO | 2018155260 | 8/2018 |

OTHER PUBLICATIONS

Extended European Search Report issued for European Patent Application No. 19823211.8, dated Sep. 27, 2021, 6 pages.

Yuge, T. et al., "Topological Classification and Supramolecular Chirality of 21-Helical Ladder-Type Hydrogen-Bond Networks Composed of Primary Ammonium Carboxylates: Bundle Control in 21-Helical Assemblies," Chemistry—A European Journal, 14, 2008, pp. 2984-2993.

Sahoo, P. et al., "Combinatorial Library of Primaryalkylammonium Dicarboxylate Gelators: A Supramolecular Synthor Approach, " Langmuir, 2009, 25(15), pp. 8742-8750.

Fujii, H., "Free radical species generated in living body and detection thereof," Technical Journal (SCAS News), Sumika Chemical Analysis Service, Ltd., No. 2010-1, vol. 31, Feb. 26, 2010, pp. 3-6 (with Partial English translation).

International Search Report and Written Opinion issued for International Patent Application No. PCT/JP2019/016712, Date of mailing: Jul. 9, 2019, 14 pages including English translation.

\* cited by examiner

Terephthalic acid

Terephthalic acid

US 12,078,644 B2

ORGANIC SALT, HYDROXY-RADICAL SENSOR INCLUDING SAME, AND DETECTION MEDIUM

TECHNICAL FIELD

The present disclosure relates to an organic salt, a hydroxy-radical sensor including the organic salt, and a detection medium.

BACKGROUND ART

Oxygen is essential for living things on the earth. However, oxygen molecules taken into a living body are changed to reactive oxygen species by a reduction reaction in cells. Examples of the reactive oxygen species include a superoxide ($O_2\cdot-$), a hydrogen peroxide ($H_2O_2$), and a hydroxy radical ($HO\cdot$). The reactive oxygen species oxidize components, such as nucleic acid, protein, lipid, and sugar, that constitute cells. Among these, a hydroxy radical has the highest oxidizing ability and is most likely to damage cells. Hydroxy radicals in a living body are mainly generated by a decomposition reaction (a Fenton reaction) of hydrogen peroxide with $Fe^{2+}$. In recent years, it has been thought that the quantity of hydroxy radicals to be generated in a living body varies depending on the stress level of a living body. By detecting hydroxy radicals, it is possible, for example, to determine the stress level of a living body.

Non Patent Literature 1 discloses a method for detecting a hydroxy radical based on an electron spin resonance (ESR) method. In the detection method of Non Patent Literature 1, a spin-trapping agent such as 5,5-dimethyl-1-pyrroline-N-oxide (DMPO) is used. More specifically, the detection method of Non Patent Literature 1 detects a hydroxy radical by analyzing DMPO-OH that is an adduct of a trapped hydroxy radical with an ESR spectrometry.

Patent Literature 1 discloses a method for detecting a hydroxy radical based on a laser-induced fluorescence (LIF) method. The detection method of Patent Literature 1 detects a hydroxy radical contained in a body surface gas diffused from a surface of a living body. More specifically, in the detection method of Patent Literature 1, a living body is irradiated with a laser beam to excite a hydroxy radical in its body surface gas, and fluorescence generated at the time when the excited hydroxy radical returns to a ground state is detected.

Patent Literature 2 discloses a method for detecting a hydroxy radical based on a p-nitrodimethylaniline method. Patent Literature 3 discloses a method for detecting a hydroxy radical based on a methional method. The detection methods of Patent Literatures 2 and 3 each require a pretreatment on a specimen containing reactive oxygen species. The pretreatment removes reactive oxygen species other than the hydroxy radical.

Patent Literature 4 discloses a method for detecting a hydroxy radical generated in a liquid, by using a terephthalic acid solution. The detection method of Patent Literature 4 utilizes fluorescence emitted from terephthalic acid that has scavenged a hydroxy radical.

Patent Literature 5 discloses a method for detecting a hydroxy radical by using a composition in which terephthalic acid or a salt thereof is carried in a base material made of a polymer gel. Patent Literature 5 discloses terephthalic acid disodium as the salt of terephthalic acid. The detection method of Patent Literature 5 utilizes fluorescence emitted from terephthalic acid that has scavenged a hydroxy radical.

CITATION LIST

Patent Literature

Patent Literature 1: JP 2013-205061 A
Patent Literature 2: JP 5(1993)-336997 A
Patent Literature 3: JP 5(1993)-336998 A
Patent Literature 4: JP 5740138 B
Patent Literature 5: JP 2018-40639 A

Non Patent Literature

Non Patent Literature 1: "Free radical species generated in living body and detection thereof", written by Hirotada Fujii, technical journal (SCAS NEWS) from Sumika Chemical Analysis Service, Ltd., No. 2010-I (Vol. 31), pages 3 to 6

SUMMARY OF INVENTION

Technical Problem

The present disclosure provides an organic salt that makes it possible to detect a hydroxy radical more easily as well as to detect a hydroxy radical generated in a living body, and a hydroxy-radical sensor adopting the organic salt.

Solution to Problem

The present disclosure provides an organic salt containing terephthalic acid and at least one kind of primary alkylamine, wherein an alkyl group constituting the primary alkylamine has 6 or more and 17 or less carbon atoms.

Advantageous Effects of Invention

The organic salt of the present disclosure makes it possible to detect a hydroxy radical more easily as well as to detect a hydroxy radical generated in a living body.

DESCRIPTION OF EMBODIMENTS (Findings on which the Present Disclosure is Based))

Detection methods based on the ESR method require to administer a spin-trapping agent to a living body. In addition, detection methods based on the ESR method or the LIF method require a large and expensive measurement analysis apparatus as well as proficient skills to detect a hydroxy radical. The detection methods of Patent Literatures 2 to 4 are based on the assumption that they detect a hydroxy radical present in a liquid. Therefore, it is difficult, as a matter of practice, to detect a hydroxy radical generated in a living body by these methods. In the detection method of Patent Literature 5, a polymer gel is used as a base material to carry terephthalic acid. The detection method of Patent Literature 5 raises a concern that the ability to detect a hydroxy radical will be lowered due to a change in composition caused, for example, by evaporation of water contained in the gel.

Terephthalic acid in a solution and a gel is a substance that can serve as a scavenging agent (a scavenger) for a hydroxy radical. As represented by the chemical formula below, terephthalic acid changes to hydroxyterephthalic acid by scavenging a hydroxy radical. Hydroxyterephthalic acid emits fluorescence having characteristics different from those of fluorescence that terephthalic acid emits. This difference in characteristics can be used to detect a hydroxy radical.

[Chemical Formula 1]

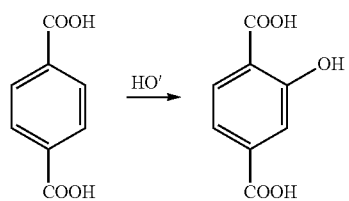

The present inventors have studied the possibility of detecting a hydroxy radical by using terephthalic acid in the form of a solid. If a hydroxy radical can be detected by using a solid, it can be considered to detect a hydroxy radical generated in a living body. This is because a hydroxy radical contained in a gas, such as a body surface gas, derived from a living body can be detected in this case. What is more, the detection based on fluorescence characteristics of a solid is noninvasive to a living body and can be carried out without using a large and expensive apparatus. That is, the detection based on fluorescence characteristics of a solid makes it possible to detect a hydroxy radical more easily.

Figure 1:
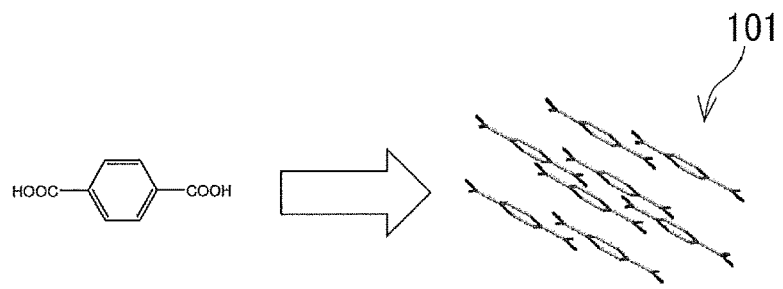
FIG. 1 is a schematic view for explaining a crystal structure of terephthalic acid.

However, the studies by the present inventors show that it is impossible to detect a hydroxy radical by using terephthalic acid in the form of a solid. Even when terephthalic acid in the form of a solid is exposed to a gas containing a hydroxy radical, the fluorescence characteristics of the terephthalic acid do not change. Presumably, this is because terephthalic acid in the form of a solid has a significantly dense crystal structure based on a $\pi$-$\pi$ stacking interaction. FIG. 1 is a schematic view for explaining a crystal structure 101 of terephthalic acid. As shown in FIG. 1, it is conceived that terephthalic acid in the form of a solid has, in its crystal structure, no cavities that can scavenge a hydroxy radical.

Through further studies, the present inventors have found, instead of a simple terephthalic acid, an organic salt containing terephthalic acid and at least one kind of primary alkylamine. This organic salt makes it possible to detect a hydroxy radical even though the organic salt is a solid. Presumably, this is because the primary alkylamine generates, in the crystal structure of the terephthalic acid, a cavity that can scavenge a hydroxy radical. It should be noted that an alkyl group constituting the primary alkylamine has 6 or more and 17 or less carbon atoms. When the number of carbon atoms is five or less, the above-mentioned cavity probably fails to be generated, making it difficult to detect a hydroxy radical. When the number of carbon atoms is 18 or more, the ratio of the terephthalic acid, in a unit weight of the organic salt, that is a scavenging agent for a hydroxy radical is low. In addition, when the number of carbon atoms is 18 or more, the organic salt is highly hydrophobic despite of the fact that a hydroxy radical is hydrophilic. Thus, when the number of carbon atoms is 18 or more, the scavenging of a hydroxy radical is probably limited, making it difficult to detect the hydroxy radical.

The organic salt of the present disclosure is a substance that makes it possible to detect a hydroxy radical more easily as well as to detect a hydroxy radical generated in a living body. The organic salt of the present disclosure makes it possible to construct a hydroxy-radical sensor that can detect a hydroxy radical more easily and can detect a hydroxy radical generated in a living body, for example.

Summary of One Aspect According to the Present Disclosure

A first aspect of the present disclosure provides an organic salt containing terephthalic acid and at least one kind of primary alkylamine. An alkyl group constituting the primary alkylamine has 6 or more and 17 or less carbon atoms.

A second aspect of the present disclosure, for example, in the organic salt as set forth in the first aspect, the alkyl group may be a normal alkyl group. The organic salt of the second aspect can have an inhibited deliquescency, for example. Thereby, the organic salt of the second aspect is advantageous in constructing a hydroxy-radical sensor, for example.

A third aspect of the present disclosure, for example, in the organic salt as set forth in the first or second aspect, the alkyl group may have 8 or more carbon atoms. The organic salt of the third aspect can have an inhibited deliquescency, for example. In addition, the organic salt of the third aspect can have an improved sensitivity to detect a hydroxy radical, for example. Thereby, the organic salt of the third aspect is advantageous in constructing a hydroxy-radical sensor, for example.

A fourth aspect of the present disclosure, for example, in the organic salt as set forth in any one of the first to third aspects, the alkyl group may have 12 or less carbon atoms. The organic salt of the fourth aspect can have an improved sensitivity to detect a hydroxy radical, for example. Thereby, the organic salt of the fourth aspect is advantageous in constructing a hydroxy-radical sensor, for example.

A fifth aspect of the present disclosure, for example, in the organic salt as set forth in any one of the first to forth aspects, the organic salt may have a supramolecular crystal structure including a molecule of the primary alkylamine and a molecule of the terephthalic acid. The organic salt of the fifth aspect can have an improved sensitivity to detect a hydroxy radical, for example. Thereby, the organic salt of the fifth aspect is advantageous in constructing a hydroxy-radical sensor, for example.

A sixth aspect of the present disclosure, for example, in the organic salt as set forth in the fifth aspect, the organic salt may have a void between the molecule of the primary alkylamine and the molecule of the terephthalic acid. The organic salt of the sixth aspect can have an improved sensitivity to detect a hydroxy radical, for example. Thereby, the organic salt of the sixth aspect is advantageous in constructing a hydroxy-radical sensor, for example.

A seventh aspect of the present disclosure, for example, in the organic salt as set forth in any one of the first to sixth aspects, the organic salt may be for detecting a hydroxy radical contained in a gas.

An eighth aspect of the present disclosure provides a hydroxy-radical sensor configured to detect a hydroxy radical contained in a gas. The hydroxy-radical sensor includes: an exposure unit that includes the organic salt as set forth in any one of the first to seventh aspects and has a structure in which the organic salt can be in contact with the gas; a light source configured to irradiate the organic salt of the exposure unit with ultraviolet light; and a light detector configured to detect fluorescence generated from the organic salt by the irradiation with the ultraviolet light. The hydroxy-radical sensor detects the hydroxy radical contained in the gas based on the fluorescence detected by the light detector.

A ninth aspect of the present disclosure, for example, in the hydroxy-radical sensor as set forth in the eighth aspect, the exposure unit may be detachable as a detection medium. The ninth aspect can make it easy to replace the organic salt in the hydroxy-radical sensor, for example. The ninth aspect can improve accuracy in detecting a very small quantity of hydroxy radicals generated in a living body by, for example, allowing the detection medium that is the exposure unit to be in contact with a living body for a predetermined period of time.

A tenth aspect of the present disclosure provides a detection medium configured to be used for detecting a hydroxy radical contained in a gas. The detection medium includes the organic salt as set forth in any one of the first to seventh aspects and has a structure in which the organic salt can be in contact with the gas. The detection medium of the tenth aspect can be used for the hydroxy-radical sensor of the ninth aspect, for example.

Embodiments of the Present Disclosure

[Organic Salt]

An organic salt of the present disclosure will be explained.

The organic salt of the present disclosure contains terephthalic acid and at least one kind of primary alkylamine. The organic salt of the present disclosure contains one to five kinds of primary alkylamines, for example, and it may contain one to three kinds of primary alkylamines and it may contain one or two kinds of primary alkylamines.

In the organic salt of the present disclosure, the terephthalic acid and the primary alkylamine are bonded to each other by an ionic bond, for example. The compositional ratio of the terephthalic acid and the primary alkylamine in the organic salt of the present disclosure is usually 1:2 based on the valence of each of them. However, the organic salt of the present disclosure may contain a higher or lower ratio of the primary alkylamine than the above-mentioned compositional ratio of 1:2. The compositional ratio of the terephthalic acid and the primary alkylamine in the organic salt of the present disclosure may be in the range of 1:0.5 to 1:4, for example.

The organic salt of the present disclosure is usually a crystalline organic salt having a crystal structure including the terephthalic acid and the primary alkylamine. The organic salt of the present disclosure may have a supramolecular crystal structure including a molecule of the primary alkylamine and a molecule of the terephthalic acid. In this case, the organic salt of the present disclosure is a supramolecular crystalline. In the present description, the term "supramolecular" refers to a regular array structure obtained by a noncovalent bond of two or more kinds of molecules. The noncovalent bond is an ionic bond, a hydrogen bond, and a π-π interaction, for example.

The organic salt of the present disclosure is usually a solid at an ordinary temperature (25° C.). However, the organic salt of the present disclosure has deliquescency in some cases. In the present description, the term "deliquescency" refers to deliquescency with respect to water vapor. The organic salt of the present disclosure that is a solid may have a high stability and preservability. In addition, the organic salt of the present disclosure that is a solid can achieve a state in which a hydroxy radical is scavenged by a solid phase, for example. This state makes it possible to maintain the scavenged hydroxy radical stably for a long time, for example. Thus, the organic salt of the present disclosure that is a solid is expected to exert effects such that: the organic salt is applicable to a detection medium to be described later; a hydroxy radical can be detected even in a certain period of time after being scavenged; and the accuracy in measuring the hydroxy radical is improved by increasing time for scavenging the hydroxy radical.

The organic salt of the present disclosure has, in its crystal structure, a void in which a hydroxy radical can be scavenged. The void may be present in a surface of the crystal structure or may be present inside the crystal structure. The void that is present inside the crystal structure is, for example, a void present between molecules that are a molecule of the primary alkylamine and a molecule of the terephthalic acid in the supramolecular crystal structure. The void usually has a size of 1 nm or less. The size of the void can be about 0.2 nm to 0.5 nm. The presence and size of the void in the crystal structure can be determined, for example, by an X-ray crystal structure analysis on the organic salt.

An alkyl group constituting the primary alkylamine has six or more carbon atoms. The alkyl group may have a branch. The alkyl group may be a normal alkyl group having no branches. In the case where the alkyl group is a normal alkyl group, the deliquescency of the organic salt can be inhibited. The inhibition of the deliquescency allows the organic salt to achieve the above-mentioned effects more reliably, for example. The alkyl group may have eight or more carbon atoms. In the case when the alkyl group has eight or more carbon atoms, the deliquescency of the organic salt can be inhibited. Presumably, the inhibition of the deliquescency is caused by formation of a hydrophobic block based on alkyl chains that linearly extend in the same direction. Also, in the case when the alkyl group has eight or more carbon atoms, the property of the organic salt to scavenge a hydroxy radical can be improved. Presumably, the improvement of the scavenging property is caused by the formation of a void between molecules based on the alkyl groups that extend linearly in the same direction. The upper limit of the number of the carbon atoms of the alkyl group is 17 or less. The alkyl group may have 12 or less carbon atoms. In the case when the alkyl group has 12 or less carbon atoms, the property of the organic salt to scavenge a hydroxy radical can be improved. In a typical example of the organic salt, hydrogen atoms bonded to the carbon atoms constituting the alkyl group are not substituted. However, at least one of the hydrogen atoms bonded to the carbon atoms constituting the alkyl group may be substituted. A substituent that substitutes the above-mentioned hydrogen atoms is a fluorine atom, for example.

Figure 2:
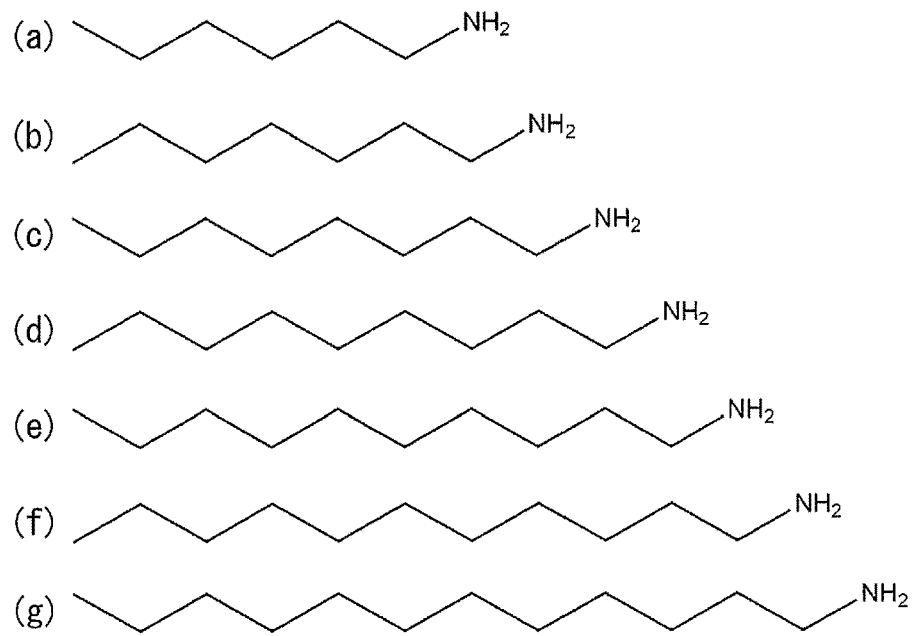
FIG. 2 is a diagram illustrating examples of primary alkylamine that an organic salt of the present disclosure can contain.

FIG. 2 shows specific examples of the primary alkylamine. The primary alkylamines shown in FIG. 2 have a normal alkyl group (an n-alkyl group). The primary alkylamines shown in FIG. 2 are, in the order of (a) to (g), n-hexylamine, n-heptylamine, n-octylamine, n-nonylamine, n-decylamine, n-undecylamine, and n-dodecylamine.

The organic salt of the present disclosure may include a molecule other than those of the terephthalic acid and the primary alkylamine.

The organic salt of the present disclosure can be in the form of powder, a pellet, a film, or a membrane, for example. However, the form of the organic salt of the present disclosure is not limited to the above-mentioned examples.

The organic salt of the present disclosure is applicable to detect a hydroxy radical, for example. In other words, the organic salt of the present disclosure may be an organic salt for detecting a hydroxy radical. However, the intended use of the organic salt of the present disclosure is not limited to the detection of a hydroxy radical.

The organic salt of the present disclosure can be obtained, for example, by adding the primary alkylamine to a mixed solution obtained by mixing the terephthalic acid with a solvent, and then distilling off the solvent therefrom. Examples of the solvent include alcohols such as methanol and ethanol.

The obtained organic salt may be turned into a solution, a dispersion, or a slurry and then undergo a forming process, for example. Through the forming process, it is possible to form a shaped body containing the organic salt. It is possible, for example, to form the organic salt that is powder, or to form powder that is a shaped body containing the organic salt, by spray-drying the solution, dispersion, or slurry of the organic salt. Also, it is possible to form the organic salt that is a membrane or a film, or to form a membrane or film that is a shaped body containing the organic salt, by drying a coating obtained by applying the solution, dispersion, or slurry of the organic salt onto a substrate. For the application onto the substrate, there can be used various kinds of techniques such as spin coating, use of a dispenser, inkjetting, and 3D printing. The shaped body may contain a material other than the organic salt. Examples of the material other than the organic salt include a binder for the organic salt. For example, in the case where the solution, dispersion, or slurry contains a binder for the organic salt, the shaped body formed can contain the binder.

[Hydroxy-Radical Sensor]

Figure 3:
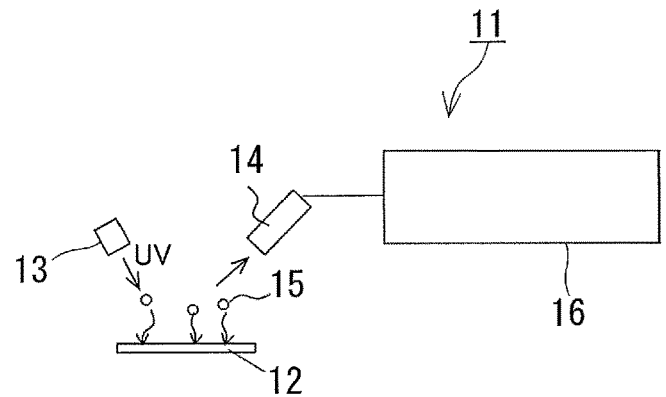
FIG. 3 is a schematic view illustrating an example of a hydroxy-radical sensor of the present disclosure.

FIG. 3 shows an example of a hydroxy-radical sensor of the present disclosure. A hydroxy-radical sensor 11 shown in FIG. 3 is configured to detect a hydroxy radical contained in a gas. The hydroxy-radical sensor 11 includes an exposure unit 12, a light source 13, and a light detector 14. The exposure unit 12 includes the organic salt of the present disclosure. The exposure unit 12 has a structure in which the organic salt can be in contact with a gas containing a hydroxy radical 15. The light source 13 irradiates the organic salt of the exposure unit 12 with ultraviolet light. The light detector 14 detects fluorescence generated from the organic salt by the irradiation with the ultraviolet light. The hydroxy-radical sensor 11 detects a hydroxy radical contained in the gas based on the fluorescence detected by the light detector 14. For that purpose, the hydroxy-radical sensor 11 shown in FIG. 3 further includes a processing unit 16 connected to the light detector 14. The processing unit 16 includes a semiconductor chip and/or a processor, for example.

More specifically, the hydroxy-radical sensor 11 can detect a hydroxy radical based on a change in the fluorescence emitted from the organic salt of the exposure unit 12. The change in the fluorescence is, for example, a difference between a fluorescence spectrum A emitted from the organic salt that has not yet scavenged a hydroxy radical and a fluorescence spectrum B emitted from the organic salt that has scavenged a hydroxy radical. The change in the fluorescence may be a change between the fluorescence spectrum A and the fluorescence spectrum B at a peak intensity. Also, the change in the fluorescence may be a change in intensity between the fluorescence spectrum A and the fluorescence spectrum B at a specific wavelength. The organic salt of the present disclosure that has scavenged a hydroxy radical can exhibit a change in fluorescence spectrum at a wavelength in the range of 385 nm to 650 nm, typically at a wavelength of 490 nm, depending on its specific composition. In other words, a hydroxy radical may be detected by detecting the change in intensity at a wavelength in the range of 385 nm to 650 nm, typically at a wavelength of 490 nm. Typically, the change in intensity is an increase in intensity. The hydroxy-radical sensor 11 can detect the quantity or concentration of hydroxy radicals contained in a gas based on the change in the fluorescence spectrum emitted from the organic salt of the exposure unit 12 by referring to a correlation data between the level of change in fluorescence and the quantity or concentration of hydroxy radicals. For that purpose, the hydroxy-radical sensor 11 may further include a storage unit that stores the correlation data. The correlation data may be stored in a storage device, such as a server, that is external to the sensor.

The ultraviolet light emitted from the light source 13 has a wavelength in the range of 300 nm to 400 nm, for example. As the light source 13, it is possible to select any light source that can emit ultraviolet light having a wavelength in the above-mentioned range.

The light detector 14 is a spectroscope, for example. The light detector 14 that is a spectroscope makes it possible to obtain an optical spectrum of fluorescence relatively easily.

In the exposure unit 12 of the hydroxy-radical sensor 11 shown in FIG. 3, the organic salt may be in any one of the forms (1) to (4) below, for example.

(1) The exposure unit 12 includes a substrate having a surface with a recess, and the recess of the substrate is filled with powder of the organic salt. The substrate is formed, for example, of glass, quartz, silicon, a silicon oxide, a metal, a metal oxide, a compound semiconductor, a resin, or a composite material thereof. The resin is, for example, a fluororesin such as polytetrafluoroethylene, and an acrylic resin such as polymethylmethacrylate.

(2) A pellet obtained by solidifying powder of the organic salt. The powder may be solidified with a binder.

(3) The exposure unit 12 includes a substrate, and a film or membrane of the organic salt is disposed on a surface of the substrate. Examples of the material that can form the substrate are the same as in (1). The method for forming the film or membrane of the organic salt is as described above.

Known members can be used as the light detector 14 and the processing unit 16.

The hydroxy-radical sensor 11 shown in FIG. 3 is just an example. The hydroxy-radical sensor of the present disclosure can have any configuration as long as it can detect a hydroxy radical. In addition, the hydroxy-radical sensor of the present disclosure may include any member other than those mentioned above as long as it can detect a hydroxy radical.

Figure 4:
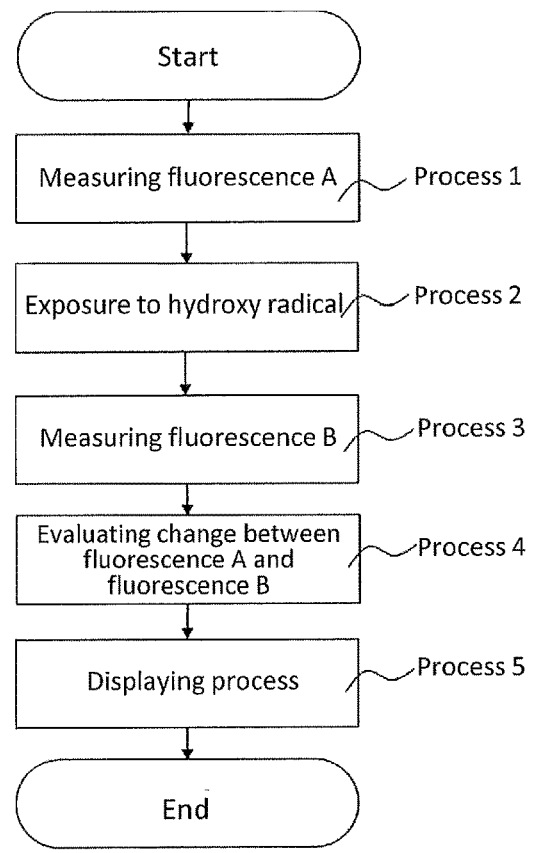
FIG. 4 is a flow chart illustrating an example of a method for detecting a hydroxy radical with the hydroxy-radical sensor of the present disclosure.

The hydroxy-radical sensor of the present disclosure detects a hydroxy radical according to the flow chart shown in FIG. 4, for example. First, the organic salt of the exposure unit 12 is irradiated with ultraviolet light emitted from the light source 13, and the fluorescence spectrum A of the organic salt that has not yet been exposed to a gas containing a hydroxy radical is measured (process of measuring the fluorescence A: Process 1). Next, the organic salt of the exposure unit 12 is exposed to the gas containing a hydroxy radical (exposure process: Process 2). Then, the organic salt that has undergone the exposure process is irradiated with ultraviolet light emitted from the light source 13, and the fluorescence spectrum B of the organic salt that has been exposed to the gas containing a hydroxy radical is measured (process for measuring the fluorescence B: Process 3). Subsequently, a change between the fluorescence spectrum A and the fluorescence spectrum B is evaluated by the processing unit 16 (evaluation process: Process 4). The evaluation results from the process 4 are displayed on a display of the processing unit 16 in the form of a numerical data, a graph, or a distribution chart (displaying process: Process 5). The hydroxy radical can be detected through these processes. The results displayed on the display are, for example, the quantity and/or concentration of hydroxy radicals contained in the gas.

The hydroxy-radical sensor of the present disclosure makes it possible to detect a hydroxy radical in a living body by a non-invasive technique, for example. For that purpose, the exposure unit 12 is exposed to a body surface gas of a living body, for example. A detection medium that can be in contact with a body surface of a living body may be used as described later.

Examples of the living body include a human, an animal, and a plant. However, the living body is not limited to the above-mentioned examples.

It is conceivable to use the hydroxy-radical sensor of the present disclosure for the following applications, for example, based on the fact that a hydroxy radical in a living body can be detected by a non-invasive technique.

(1) Applications to prevention of presymptomatic states, early diagnosis, early treatment and evaluation on treatment effects, related to various oxidative stress diseases. These applications can be practiced in a wide range of medical care settings such as examination, outpatient treatment, and bedside treatment.

(2) Substitution for conventional oxidative stress markers. Conventional oxidative stress markers detect a hydroxy radical by utilizing chemical modification by the hydroxy radical.

(3) Monitoring on generation of a hydroxy radical in a living body. There is a possibility that this monitoring can be practiced in various clinical settings such as evaluation on treatment effects and emergency care. Diseases to be subject to the monitoring are, for example, ischemic and reperfusion disorders such as chronic fatigue syndrome, cerebral infarction, myocardial infarction, and angina pectoris.

(4) Applications to health maintenance and enhancement. For example, application to instruction or supervision on various items such as nutritional status, the quantity of physical activities, sleep, leisure, and lifestyle.

(5) Applications to sports medicine based on detection of a hydroxy radical generated by exercising.

Use of the hydroxy-radical sensor of the present disclosure is not limited to detection of a hydroxy radical in a living body, and it can be used for various applications to detect a hydroxy radical contained in a gas. An example of the applications is to detect a hydroxy radical released from a plasma process or ultraviolet light process into a gas. This detection makes it possible to control the plasma process and ultraviolet light process more precisely.

In the hydroxy-radical sensor of the present disclosure, the exposure unit 12 can be detachable as a detection medium. In this case, the organic salt can be replaced easily in the hydroxy-radical sensor, for example. Also, in this case, it is possible to improve the accuracy in detecting a very small quantity of hydroxy radicals generated in a living body by, for example, allowing the detection medium that is the exposure unit to be in contact with a living body for a predetermined period of time. The detection medium is a detection medium of the present disclosure, for example.

[Detection Medium]

Figure 5:
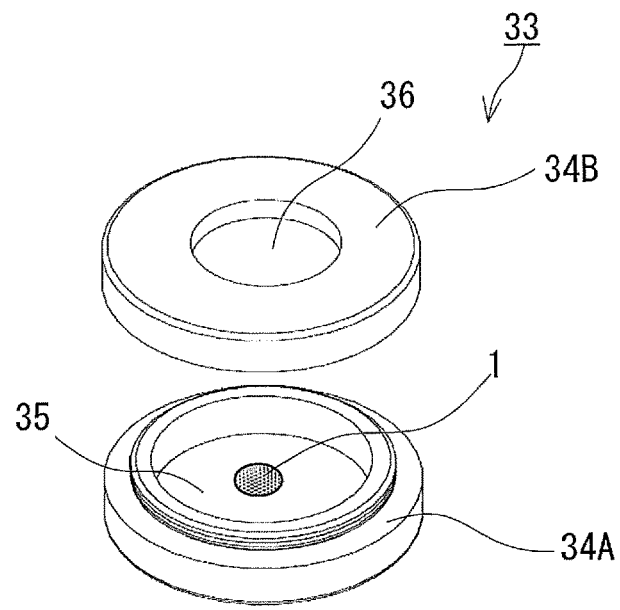
FIG. 5 is a perspective view schematically illustrating an example of a detection medium of the present disclosure.

FIG. 5 is a perspective view illustrating an example of the detection medium of the present disclosure. A detection medium 33 shown in FIG. 5 includes a body part 34A, a cover 34B, and an organic salt 1 placed on a bottom surface 35 of the body part 34A. The body part 34A and the cover 34B can be joined to each other by being screwed together. The cover 34B has a through hole 36. A gas can flow into the detection medium 33 via the through hole 36 in the state where the body part 34A and the cover 34B are screwed to each other. In other words, the detection medium 33 has a structure in which the organic salt 1 can be in contact with the gas that has flown into the detection medium 33 via the through hole 36. The organic salt 1 is a pellet of the organic salt 1, for example. However, the form of the organic salt 1 included in the detection medium 33 is not limited to a pellet.

The body part 34A and the cover 34B can be formed of a material such as a metal and a resin. Examples of the metal include aluminum and stainless steel. Examples of the resin include a fluororesin such as polytetrafluoroethylene. However, the material which the body part 34A and the cover 34B are formed of is not limited to the above-mentioned examples.

The detection medium 33 can be used as it is. However, the state of use of the detection medium 33 is not limited. The detection medium 33 can be used in the state of being fixed to a belt imitating a band of a wrist watch, for example.

The detection medium of the present disclosure may have any structure as long as it includes the organic salt of the present disclosure and has a structure in which the organic salt can be in contact with a gas containing a hydroxy radical to be detected. The detection medium of the present disclosure may have any member as long as it includes the organic salt of the present disclosure and has a structure in which the organic salt can be in contact with a gas containing a hydroxy radical to be detected.

EXAMPLES

Hereinafter, the organic salt and the hydroxy-radical sensor of the present disclosure will be described in detail with reference to Examples. The organic salt and the hydroxy-radical sensor of the present disclosure are not limited to the aspects described in detail in the following Examples.

Example 1

[Synthesis of Organic Salt]

In Example 1, a terephthalic acid bis(n-octylamine) salt was synthesized as an organic salt by the following procedure. First, 1.00 g (6.02 mmol) of terephthalic acid was mixed with methanol to obtain 100 mL of a mixed solution of the terephthalic acid and the methanol. Next, 1.95 g (15.05 mmol) of n-octylamine was poured into the mixed solution under a room temperature. Subsequently, the resulting mixed solution was stirred at a room temperature, and then the methanol was distilled off therefrom under a reduced pressure. Thereafter, diethyl ether was added to the obtained residue and the entirety was stirred at a room temperature, and then it was filtered under a reduced pressure and dried to obtain 2.49 g (5.86 mmol) of a terephthalic acid bis(n-octylamine) salt.

[Evaluation on Crystal Structure of Terephthalic Acid Bis (n-Octylamine) Salt]

Figure 6:
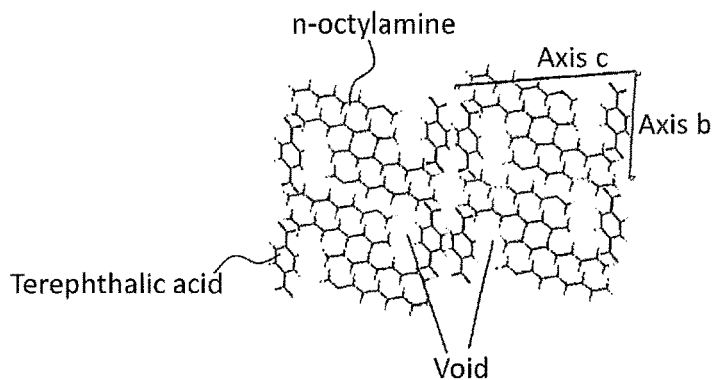
FIG. 6 is a schematic view illustrating a crystal structure of a terephthalic acid bis(n-octylamine) salt produced in Example 1.

A crystal structure of the produced terephthalic acid bis(n-octylamine) salt was evaluated by an X-ray crystal structure analysis. FIG. 6 shows the crystal structure observed by the evaluation. As shown in FIG. 6, the terephthalic acid bis(n-octylamine) salt was found to have the following crystal structure.

(1) A supramolecular crystal structure composed of a molecule of the terephthalic acid and a molecule of the n-octylamine was constructed. The compositional ratio was 1:2.

(2) An n-octyl chain that each n-octylamine molecule had extended linearly. In addition, the n-octyl chains that a plurality of the n-octylamine molecules respectively had were arrayed parallel to each other.

(3) A plurality of the n-octyl chains arrayed parallel to each other formed a hydrophobic block.

(4) A plurality of voids having a size of 1 nm or less were present between the molecule of the terephthalic acid and the molecule of the n-octylamine.

[Evaluation on Ability of Terephthalic Acid Bis(n-Octylamine) Salt to Detect Hydroxy Radical]

The produced terephthalic acid bis(n-octylamine) salt was evaluated for ability to detect a hydroxy radical according to the following procedure.

<Filling Specimen Holder>

Figure 7:
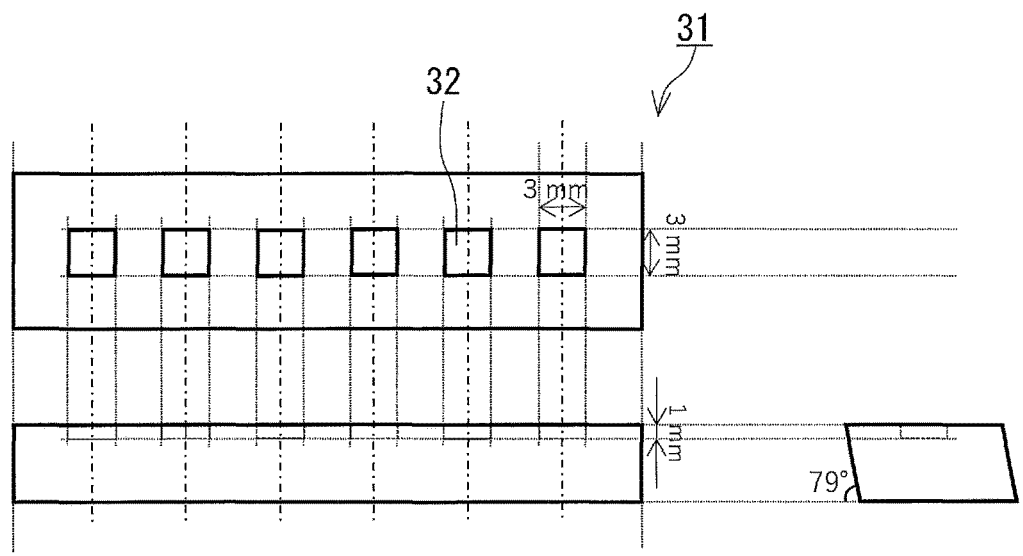
FIG. 7 is a three-view diagram schematically illustrating a specimen holder used for evaluating organic salts produced in Examples and Comparative Examples.

A specimen holder 31 shown in FIG. 7 was prepared. FIG. 7 is a three-view diagram schematically illustrating the specimen holder used for evaluating the organic salts produced in Examples and Comparative Examples. The specimen holder 31 was an oblique quadrangular prism made of polytetrafluoroethylene. It should be noted that the angle between a bottom surface of the oblique quadrangular prism and each of two side surfaces, out of four side surfaces of the oblique quadrangular prism, that faced each other and had a relatively large area was set to an angle 11 degrees off from a right angle. An upper surface of the oblique quadrangular prism had six recesses 32. Each of the recesses 32 had a 3 mm×3 mm square opening and a depth of 1 mm. Each of the recesses 32 of the prepared specimen holder 31 was filled with the produced terephthalic acid bis(n-octylamine) salt. The filling quantity was 3.5 to 4 mg for each of the recesses 32.

<Measurement of Fluorescence Spectrum A>

Figure 8:
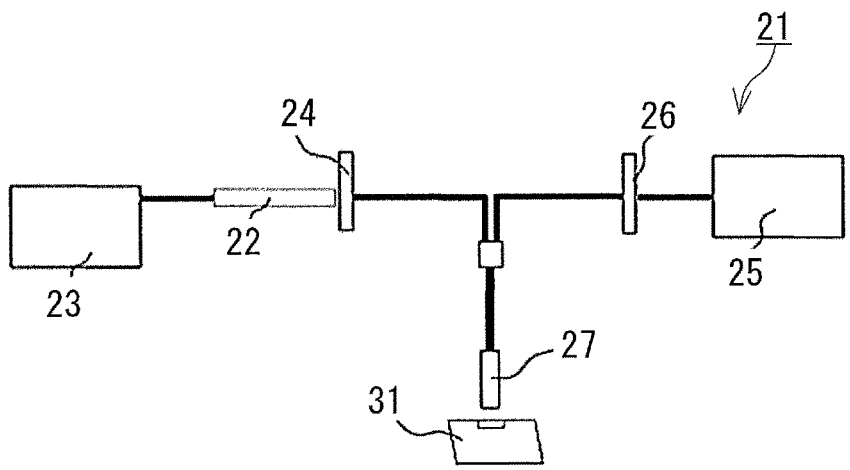
FIG. 8 is a schematic view illustrating an optical system used for evaluating the organic salts produced in Examples and Comparative Examples.

An optical system 21 shown in FIG. 8 was prepared. FIG. 8 is a schematic view illustrating the optical system used for evaluating the organic salts produced in Examples and Comparative Examples. The optical system 21 included a light source 22, a power supply 23, a band pass filter 24, a spectroscope 25, a long pass filter 26, and a probe 27. The light source 22 was a light source of ultraviolet light. As the light source 22, an ultraviolet LED light source (LED-UV (12)) available from SUGITOH Co., Ltd. was used. As the power supply 23 for the light source 22, an LED power supply (JOL-1205AICT) available from SUGITOH Co., Ltd. was used. The band pass filter 24 was used to irradiate the organic salt only with ultraviolet light having a wavelength in the range of 360 nm to 370 nm. As the band pass filter 24, YIF-BP360-370S available from SIGMAKOKI CO., LTD. was used. The probe 27 was used to irradiate the organic salt filling the specimen holder 31 with the ultraviolet light as well as to guide fluorescence emitted from the organic salt by the irradiation with the ultraviolet light to the spectroscope 25. As the probe 27, a reflection/backscattering probe (R400-7-UV-VIS available from Ocean Optics, Inc.) was used. The distance between a tip of the probe 27 and the organic salt filling the specimen holder 31 was set to 3 mm. As the spectroscope 25, a spectrometer system SEC2000-UV/VI available from BAS Inc. was used. The long pass filter (short wavelength cut-off filter) 26 was used in order not to introduce light having a wavelength of less than 385 nm to the spectroscope 25. As the long pass filter 26, LUX385 available from Asahi Spectra Co., Ltd. was used.

The fluorescence spectrum A of the terephthalic acid bis(n-octylamine) salt that had not yet been exposed to a gas containing a hydroxy radical was measured using the prepared optical system 21. The measurement of the fluorescence spectrum A was carried out on portions of the terephthalic acid bis(n-octylamine) salt respectively filling the recesses of the specimen holder 31. The average spectrum of the fluorescence spectra A obtained by the measurement was used for comparison with the fluorescence spectrum B to be described later.

<Exposure to Gas Containing Hydroxy Radical>

Figure 9:
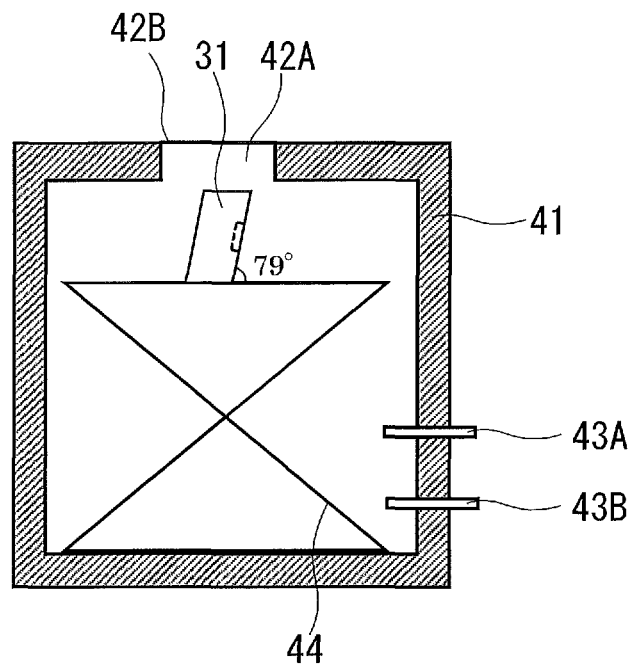
FIG. 9 is a schematic view illustrating a chamber for accommodating a specimen holder, the chamber being used for evaluating the organic salts produced in Examples and Comparative Examples.

A specimen holder accommodation chamber 41 shown in FIG. 9 was prepared. FIG. 9 is a schematic view illustrating the specimen holder accommodation chamber used for evaluating the organic salts produced in Examples and Comparative Examples. The chamber 41 had an upper face with an opening 42A. A sapphire substrate 42B was disposed at the opening 42A in such a manner as to cover the opening 42A. The sapphire substrate 42B allowed ultraviolet light having a wavelength of 254 nm and ultraviolet light having a wavelength of 185 nm emitted from an ozone lamp 45 (see FIG. 10) to pass therethrough. The sapphire substrate 42B covering the opening 42A was able to bring the chamber 41 into a sealed state. The chamber 41 had a structure that withstands a reduced pressure from 1 to several Torr in terms of absolute pressure.

The chamber 41 included nozzles 43A and 43B extending through a wall of the chamber 41. The nozzles 43A and 43B made it possible to fill an inside of the chamber 41 with nitrogen or humidified nitrogen and to allow these nitrogens to always flow in and out from the chamber 41.

A jack 44 was accommodated inside the prepared chamber 41. The jack 44 was adjusted so that a distance between the ozone lamp 45 and the specimen holder 31 was about 24 mm. Next, the specimen holder 31 filled with the organic salt was placed on an upper surface of the jack 44. The specimen holder 31 was placed so that the side surface thereof set to an angle 11 degrees off from a right angle serves as a contact surface with the upper surface of the jack 44 in order not to irradiate directly the organic salt with the ultraviolet light emitted from the ozone lamp 45 (see FIG. 9).

Figure 10:
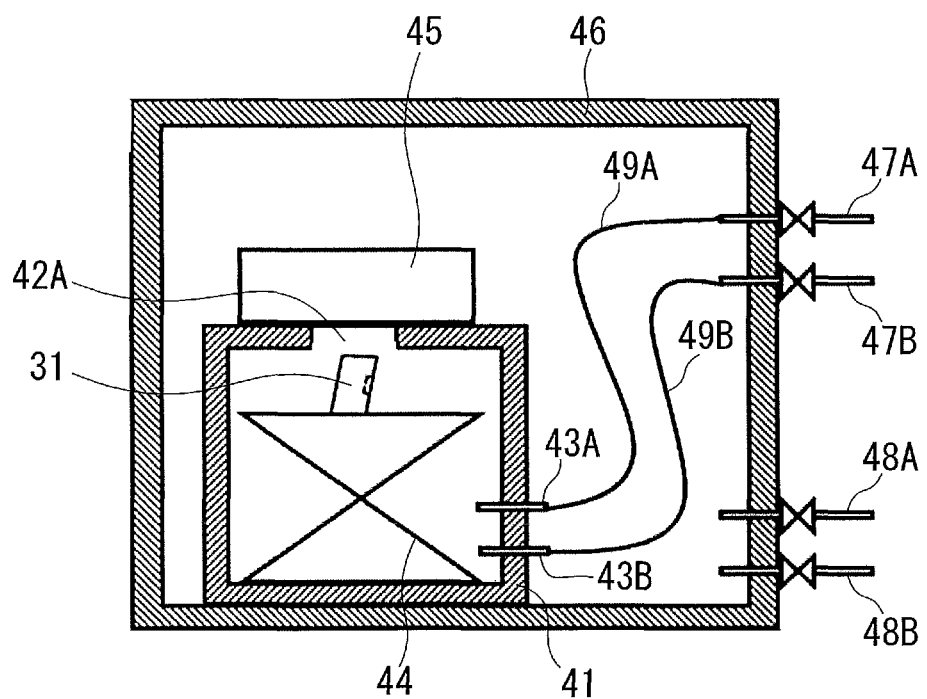
FIG. 10 is a schematic view illustrating an ultraviolet irradiation chamber used for evaluating the organic salts produced in Examples and Comparative Examples.

Next, the chamber 41 was accommodated in an ultraviolet radiation chamber 46 as shown in FIG. 10. FIG. 10 is a schematic view illustrating the ultraviolet irradiation chamber used for evaluating the organic salts produced in Examples and Comparative Examples. The chamber 46 had a structure that withstands a reduced pressure from 1 to several Torr in terms of absolute pressure. The chamber 46 included nozzles 47A and 47B as well as nozzles 48A and 48B extending through a wall of the chamber 46. The nozzles 48A and 48B made it possible to fill an inside of the chamber 46 with nitrogen and to allow the nitrogen to always flow in and out from the chamber 46. The nozzles 47A and 47B were connected respectively to the nozzles 43A and 43B of the chamber 41 with respective pipes 49A and 49B. Next, the ozone lamp 45 was disposed in such a manner as to cover the opening 42A of the chamber 41 as well as to allow the inside of the chamber 41 to be irradiated with the ultraviolet light via the opening 42A. As the ozone lamp 45, GL-4Z available from KYOKKO DENKI Co., Ltd. was used. The ozone lamp 45 was able to emit ultraviolet light having a wavelength of 254 nm and ultraviolet light having a wavelength of 185 nm.

Next, the inside of the chamber 41 and that of the chamber 46 were purged with nitrogen. The purge with nitrogen was carried out in order to prevent reactive oxygen species other than a hydroxy radical from being generated. More specifically, the pressure inside the chamber 41 and that inside the chamber 46 were reduced, and then filled the insides of these chambers with nitrogen a plurality of times. Thereafter, the quantity of humidified nitrogen to fill the chamber 41 was controlled so that the relative humidity in the chamber 41 was 90 to 93%. The temperature in the chamber 41 was controlled to 18 to 23° C.

After the temperature and the relative humidity in the chamber 41 were determined, the inside of the chamber 41 was irradiated with ultraviolet light for 2 hours using the ozone lamp 45. A vacuum ultraviolet ray (VUV) having a wavelength of 185 nm emitted from the ozone lamp 45 cut an OH bond in water, thereby generating a hydroxy radical (see Equation (1) below). Equation (1) appears, for example, on page 83 of "Generation of OH Radicals and Application Technology" published by NTS Inc. In this manner, the organic salt filling the specimen holder 31 was exposed to a gas containing a hydroxy radical.

$$H_2O + VUV185\ nm \rightarrow HO\cdot + H \tag{1}$$

<Measurement of Fluorescence Spectrum B>

Figure 11:
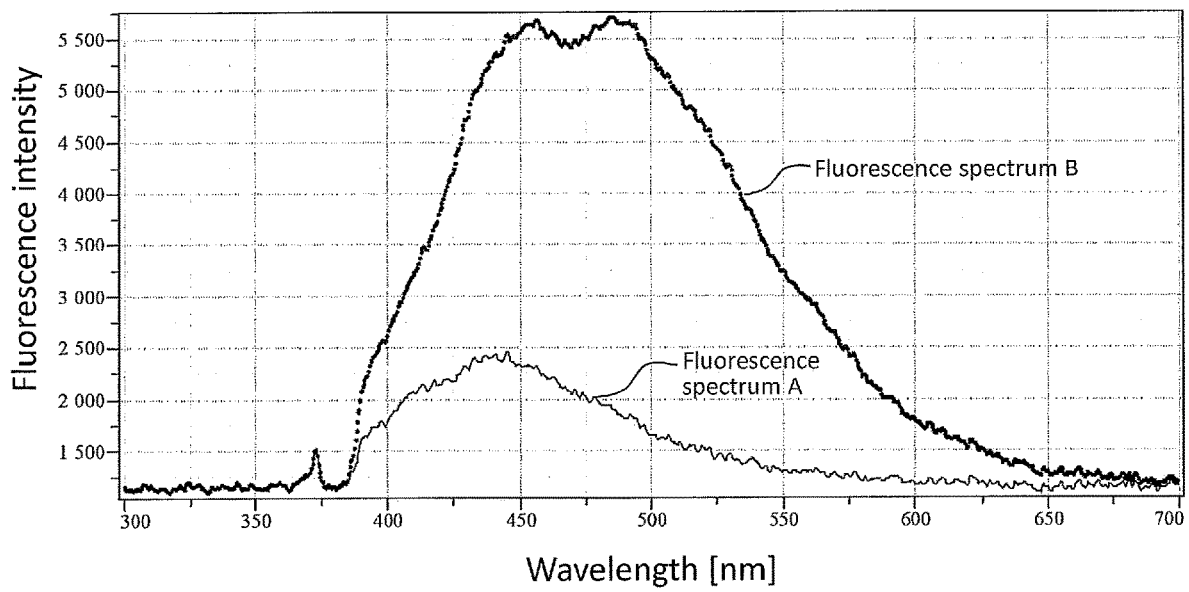
FIG. 11 is a graph showing a fluorescence spectrum A and a fluorescence spectrum B of the terephthalic acid bis(n-octylamine) salt produced in Example 1.

The fluorescence spectrum B of the terephthalic acid bis(n-octylamine) salt that had been exposed to the gas containing a hydroxy radical was measured in the same manner as the measurement of the fluorescence spectrum A. The measurement of the fluorescence spectrum B was carried out on portions of the terephthalic acid bis(n-octylamine) salt respectively filling the recesses of the specimen holder 31. The average spectrum of the fluorescence spectra B obtained by the measurement was used for comparison with the fluorescence spectrum A. Each of the fluorescence spectrum A and the fluorescence spectrum B shown in figures below is an average spectrum calculated mathematically. FIG. 11 shows the fluorescence spectrum A and the fluorescence spectrum B of the terephthalic acid bis(n-octylamine) salt. As shown in FIG. 11, the fluorescence generated, by the irradiation with the ultraviolet light, from the terephthalic acid bis(n-octylamine) salt that had been exposed to the gas containing a hydroxy radical exhibited a higher intensity over a wide wavelength range from 385 nm to 650 nm and a higher intensity at a wavelength of 490 nm than that of the terephthalic acid bis(n-octylamine) salt that had not yet been exposed to the gas containing a hydroxy radical. That is, it was confirmed that the terephthalic acid bis(n-octylamine) salt had an ability to detect a hydroxy radical.

For comparison, there was measured, in the same manner as the measurement of the fluorescence spectrum A, a fluorescence spectrum of the terephthalic acid bis(n-octylamine) salt that had been left, without being exposed to the gas containing a hydroxy radical, for 2 hours in an atmosphere controlled to have a temperature of 20° C. and a relative humidity of 91 to 93%. The measured fluorescence spectrum showed no difference from the fluorescence spectrum A.

A mass spectrometry was carried out on the terephthalic acid bis(n-octylamine) salt both before and after the exposure to the gas containing a hydroxy radical. An apparatus used for the mass spectrometry and measurement conditions of the mass spectrometry were as follows.

Apparatus: LTQ Orbitrap XL available from Thermo Fisher Scientific K.K.

Ionizing method: Electrospray ionization (ESI) method, anion mode

Figure 12:
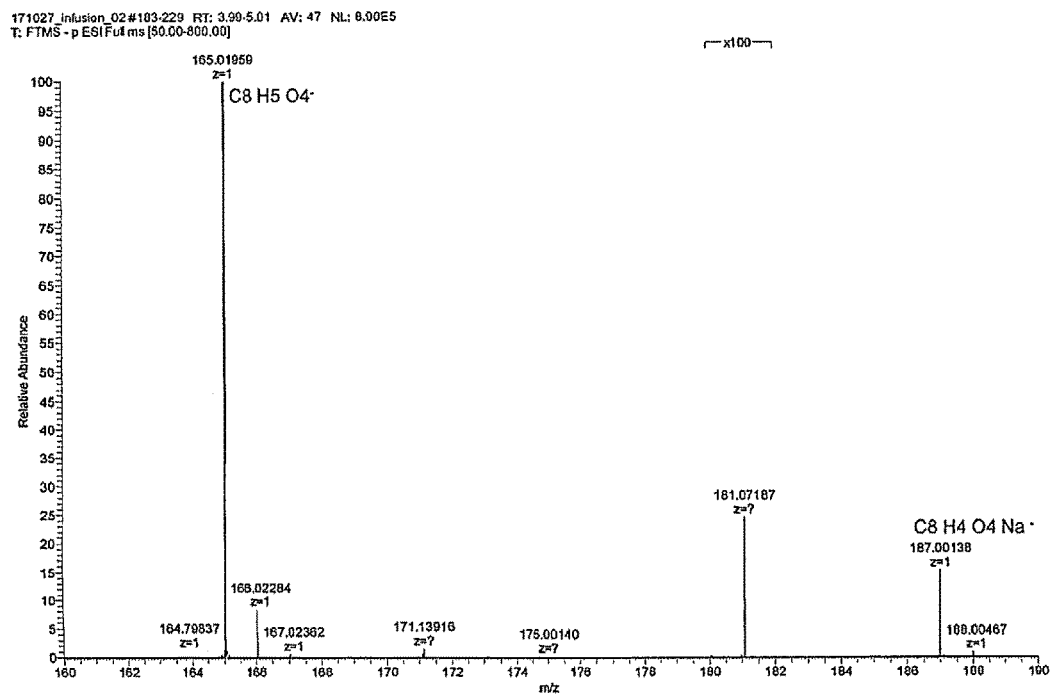
FIG. 12 is a diagram illustrating mass spectrometry results (before exposure) of the terephthalic acid bis(n-octylamine) salt produced in Example 1.
Figure 13:
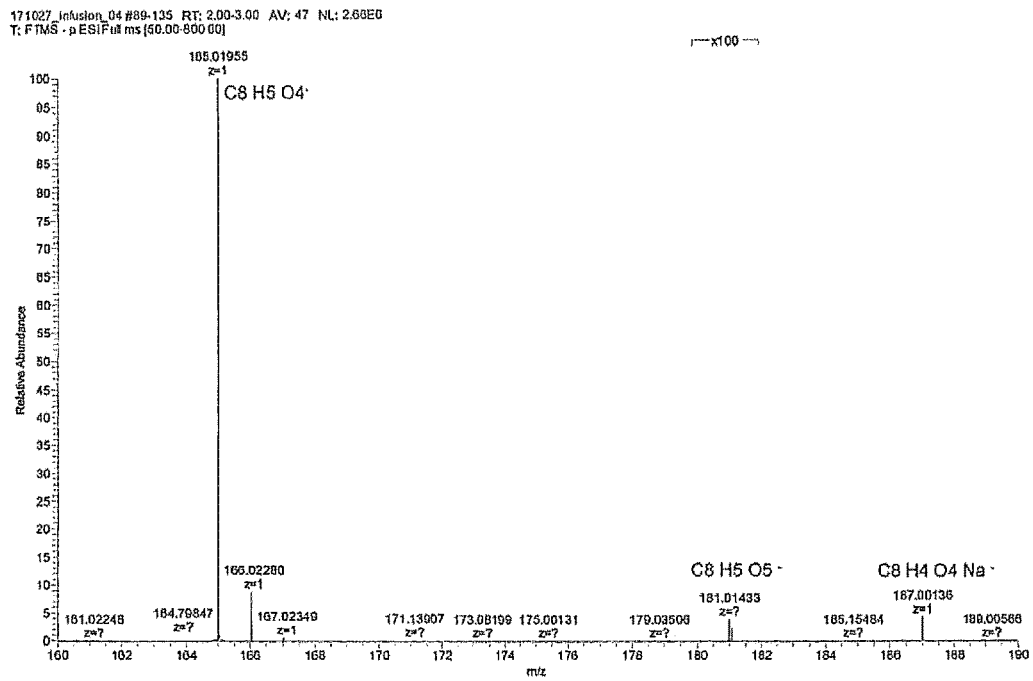
FIG. 13 is a diagram illustrating mass spectrometry results (after exposure) of the terephthalic acid bis(n-octylamine) salt produced in Example 1.

Measurement conditions: Infusion measurement using a methanol solution Spray voltage 3 kV Standard solution flow rate 5 µL/minute FIG. 12 shows the results of the mass spectrometry on the terephthalic acid bis(n-octylamine) salt before the exposure to the gas containing a hydroxy radical. FIG. 13 shows the results of the mass spectrometry on the terephthalic acid bis(n-octylamine) salt after the exposure to the gas containing a hydroxy radical. As shown in FIG. 12 and FIG. 13, the mass spectrometry after the exposure to the gas containing a hydroxy radical exhibited a value of "m/z=181.0143", which was not observed in the mass spectrometry before the exposure. The value "m/z=181.0143" corresponds to hydroxyterephthalic acid. That is, it was confirmed that a terephthalic acid molecule of the terephthalic acid bis(n-octylamine) salt was hydroxylated by the exposure to the gas containing a hydroxy radical.

[Evaluation of Deliquescency of Terephthalic Acid Bis(n-Octylamine) Salt]

The terephthalic acid bis(n-octylamine) salt was left for 2 hours in an atmosphere controlled to have a temperature of 18 to 20° C. and a relative humidity of 100%. No deliquescency was observed on the terephthalic acid bis(n-octylamine) salt that had been left. The presence or absence of deliquescency was evaluated visually.

[Experiment of Exposure to Body Surface Gas]

There was prepared a specimen holder having the same structure as that of the specimen holder 31 shown in FIG. 7, except that it had three recesses 32 and each of the recesses 32 had a 2 mm×2 mm square opening. Each of the recesses 32 of the prepared specimen holder was filled with the produced terephthalic acid bis(n-octylamine) salt. The filling quantity was 1.5 to 1.7 mg for each of the recesses 32.

Next, the specimen holder filled with the terephthalic acid bis(n-octylamine) salt was left for 2 hours while being in contact with a surface of a forearm of a person serving as a test subject via an ethylene-tetrafluoroethylene (ETFE) mesh having air permeability in a thickness direction. The specimen holder was in contact with the forearm in such a manner that the openings of the recesses 32 faced the surface of the forearm. The specimen holder was fixed to the forearm using a medical tape.

Figure 14:
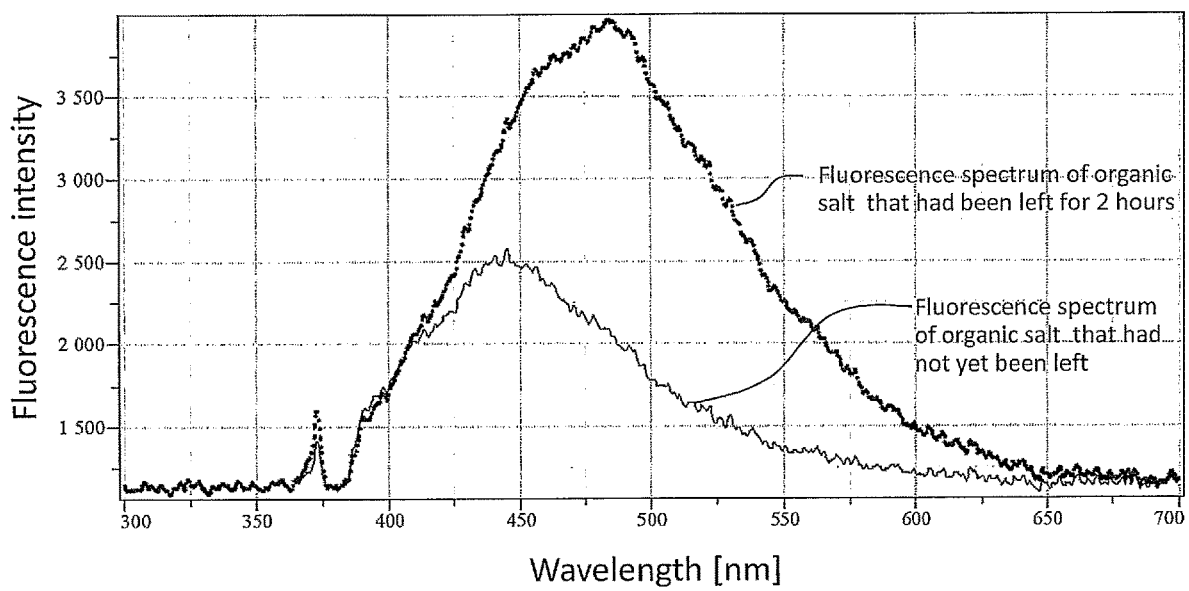
FIG. 14 is a graph showing fluorescence spectra (before and after exposure to a body surface gas) of the terephthalic acid bis(n-octylamine) salt produced in Example 1.

A fluorescence spectrum of the terephthalic acid bis(n-octylamine) salt that had not yet been left for 2 hours and a fluorescence spectrum of the terephthalic acid bis(n-octylamine) salt that had been left for 2 hours were measured in the same manner as the fluorescence spectrum A. FIG. 14 shows the measurement results of the fluorescence spectra. As shown in FIG. 14, the fluorescence generated, by the irradiation with the ultraviolet light, from the terephthalic acid bis(n-octylamine) salt that had been exposed to the body surface gas exhibited a higher intensity over a wide wavelength range from 385 nm to 620 nm and a higher intensity at a wavelength of 490 nm than that of the terephthalic acid bis(n-octylamine) salt that had not yet been left. That is, it was confirmed that the terephthalic acid bis(n-octylamine) salt had an ability to detect a hydroxy radical contained in the body surface gas.

Example 2

1.90 g (15.05 mmol) of n-nonylamine was used instead of the n-octylamine. 2.67 g (5.90 mmol) of a terephthalic acid (n-nonylamine) salt was obtained in the same manner as in Example 1 except for the above-mentioned condition.

Figure 15:
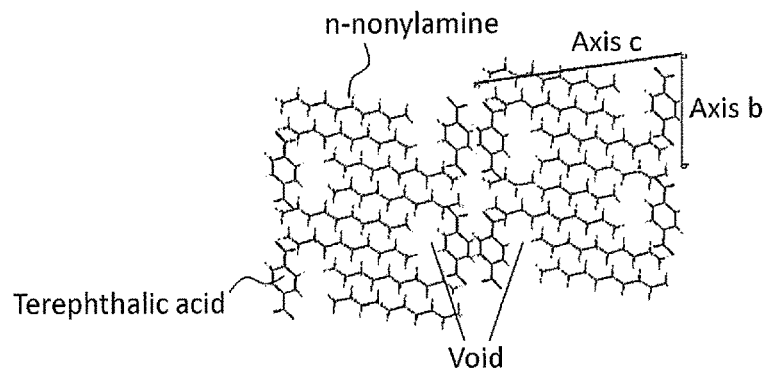
FIG. 15 is a schematic view illustrating a crystal structure of a terephthalic acid bis(n-nonylamine) salt produced in Example 2.

A crystal structure of the produced terephthalic acid (n-nonylamine) salt was evaluated by the same X-ray crystal structure analysis as in Example 1. FIG. shows the crystal structure observed by the evaluation. As shown in FIG. 15, the terephthalic acid (n-nonylamine) salt was found to have the following crystal structure.

(1) A supramolecular crystal structure composed of a molecule of the terephthalic acid and a molecule of the n-nonylamine was constructed. The compositional ratio was 1:2.

(2) An n-nonyl chain that each n-nonylamine molecule had extended linearly. In addition, the n-nonyl chains that a plurality of the n-nonylamine molecules respectively had were arrayed parallel to each other.

(3) A plurality of the n-nonyl chains arrayed parallel to each other formed a hydrophobic block.

(4) A plurality of voids having a size of 1 nm or less were present between the molecule of the terephthalic acid and the molecule of the n-nonylamine.

Figure 16:
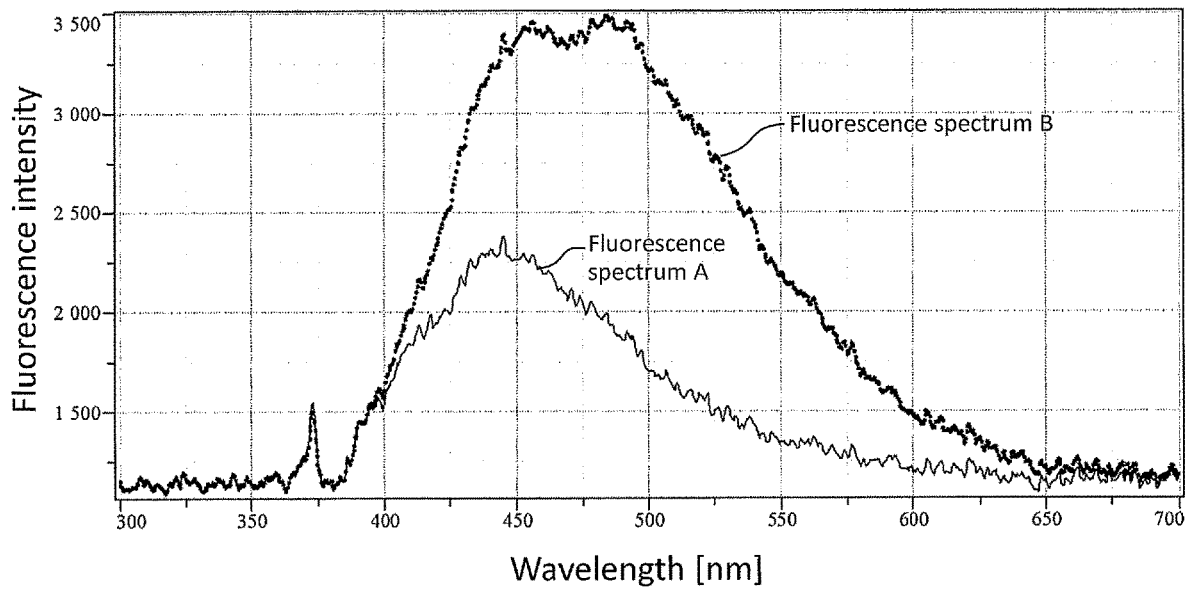
FIG. 16 is a graph showing the fluorescence spectrum A and the fluorescence spectrum B of the terephthalic acid bis(n-nonylamine) salt produced in Example 2.

The produced terephthalic acid bis(n-nonylamine) salt was evaluated for ability to detect a hydroxy radical by the same technique as in Example 1. FIG. 16 shows the fluorescence spectrum A and the fluorescence spectrum B of the terephthalic acid bis(n-nonylamine) salt. As shown in FIG. 16, the fluorescence generated, by the irradiation with the ultraviolet light, from the terephthalic acid bis(n-nonylamine) salt that had been exposed to the gas containing a hydroxy radical exhibited a higher intensity over a wide wavelength range from 385 nm to 625 nm and a greater increase in intensity at a wavelength of 490 nm than that of the terephthalic acid bis(n-nonylamine) salt that had not yet been exposed to the gas containing a hydroxy radical. That is, it was confirmed that the terephthalic acid bis(n-nonylamine) salt had an ability to detect a hydroxy radical.

For comparison, there was measured, in the same manner as the measurement of the fluorescence spectrum A, a fluorescence spectrum of the terephthalic acid bis(n-nonylamine) salt that had been left, without being exposed to the gas containing a hydroxy radical, for 2 hours in an atmosphere controlled to have a temperature of 19° C. and a relative humidity of 92 to 93%. The measured fluorescence spectrum showed no difference from the fluorescence spectrum A.

The produced terephthalic acid bis(n-nonylamine) salt was evaluated for deliquescency by the same technique as in Example 1. No deliquescency was observed on the terephthalic acid bis(n-nonylamine) salt that had been left for 2 hours in an atmosphere controlled to have a temperature of 18 to 20° C. and a relative humidity of 100%.

Example 3

The quantity of the terephthalic acid was changed to 2.00 g (12.04 mmol), and the quantity of the obtained mixed solution of the terephthalic acid and the methanol was changed to 150 mL. In addition, 4.54 g (26.49 mmol) of n-undecylamine was used instead of the n-octylamine. 5.97 g (11.73 mmol) of a terephthalic acid (n-undecylamine) salt was obtained in the same manner as in Example 1 except for the above-mentioned conditions.

Figure 17:
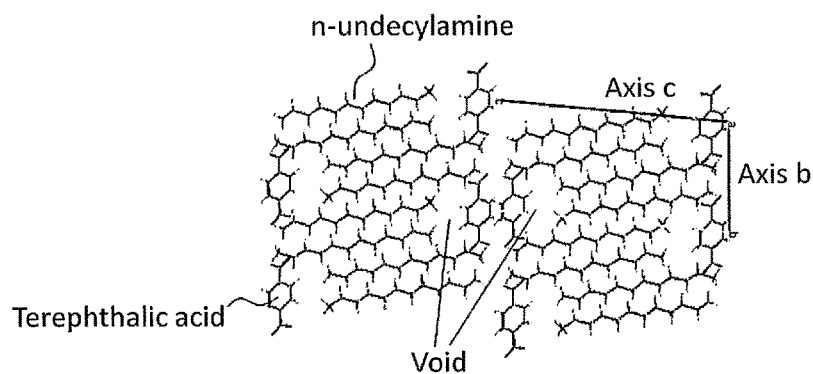
FIG. 17 is a schematic view illustrating a crystal structure of a terephthalic acid bis(n-undecylamine) salt produced in Example 3.

A crystal structure of the produced terephthalic acid (n-undecylamine) salt was evaluated by the same X-ray crystal structure analysis as in Example 1. FIG. 17 shows the crystal structure observed by the evaluation. As shown in FIG. 17, the terephthalic acid (n-undecylamine) salt was found to have the following crystal structure.

(1) A supramolecular crystal structure composed of a molecule of the terephthalic acid and a molecule of the n-undecylamine was constructed. The compositional ratio was 1:2.

(2) An n-undecyl chain that each n-undecylamine molecule had extended linearly. In addition, the n-undecyl chains that a plurality of the n-undecylamine molecules respectively had were arrayed parallel to each other.

(3) A plurality of the n-undecyl chains arrayed parallel to each other formed a hydrophobic block.

(4) A plurality of voids having a size of 1 nm or less were present between the molecule of the terephthalic acid and the molecule of the n-undecylamine.

Figure 18:
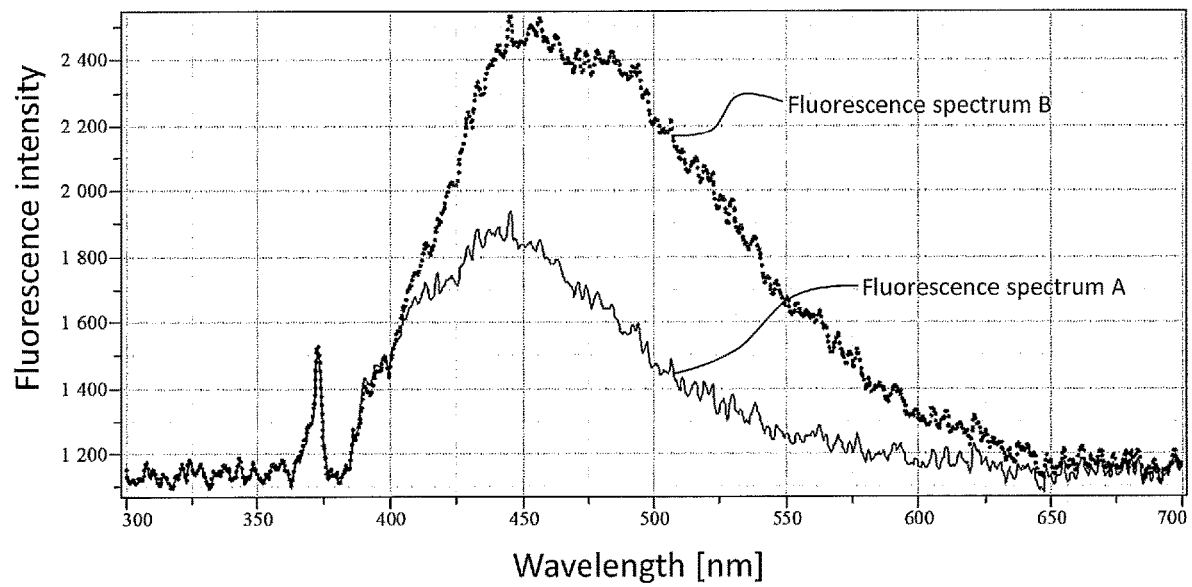
FIG. 18 is a graph showing the fluorescence spectrum A and the fluorescence spectrum B of the terephthalic acid bis(n-undecylamine) salt produced in Example 3.

The produced terephthalic acid bis(n-undecylamine) salt was evaluated for ability to detect a hydroxy radical by the same technique as in Example 1. FIG. 18 shows the fluorescence spectrum A and the fluorescence spectrum B of the terephthalic acid bis(n-undecylamine) salt. As shown in FIG. 18, the fluorescence generated, by the irradiation with the ultraviolet light, from the terephthalic acid bis(n-undecylamine) salt that had been exposed to the gas containing a hydroxy radical exhibited a higher intensity over a wide wavelength range from 385 nm to 615 nm and a higher intensity at a wavelength of 490 nm than the terephthalic acid bis(n-undecylamine) salt that had not yet been exposed to the gas containing a hydroxy radical. That is, it was confirmed that the terephthalic acid bis(n-undecylamine) salt had an ability to detect a hydroxy radical.

For comparison, there was measured, in the same manner as the measurement of the fluorescence spectrum A, a fluorescence spectrum of the terephthalic acid bis(n-undecylamine) salt that had been left, without being exposed to the gas containing a hydroxy radical, for 2 hours in an atmosphere controlled to have a temperature of 20° C. and a relative humidity of 90 to 92%. The measured fluorescence spectrum showed no difference from the fluorescence spectrum A.

The produced terephthalic acid bis(n-undecylamine) salt was evaluated for deliquescency by the same technique as in Example 1. No deliquescency was observed on the terephthalic acid bis(n-undecylamine) salt that had been left for 2 hours in an atmosphere controlled to have a temperature of 18 to 20° C. and a relative humidity of 100%.

Example 4

2.79 g (15.05 mmol) of n-dodecylamine was used instead of the n-octylamine. 3.06 g (5.70 mmol) of a terephthalic acid (n-dodecylamine) salt was obtained in the same manner as in Example 1 except for the above-mentioned condition.

Figure 19:
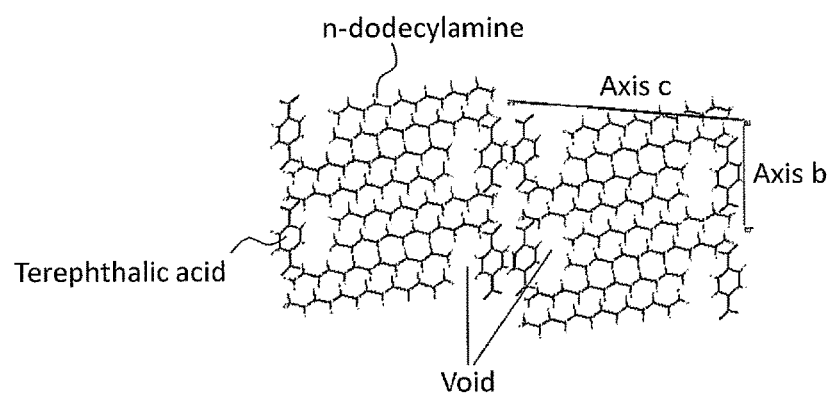
FIG. 19 is a schematic view illustrating a crystal structure of a terephthalic acid bis(n-dodecylamine) salt produced in Example 4.

A crystal structure of the produced terephthalic acid (n-dodecylamine) salt was evaluated by the same X-ray crystal structure analysis as in Example 1. FIG. 19 shows the crystal structure observed by the evaluation. As shown in FIG. 19, the terephthalic acid (n-dodecylamine) salt was found to have the following crystal structure.

(1) A supramolecular crystal structure composed of a molecule of the terephthalic acid and a molecule of the n-dodecylamine was constructed. The compositional ratio was 1:2.

(2) An n-dodecyl chain that each n-dodecylamine molecule had extended linearly. In addition, the n-dodecyl chains that a plurality of the n-dodecylamine molecules respectively had were arrayed parallel to each other.

(3) A plurality of the n-dodecyl chains arrayed parallel to each other formed a hydrophobic block.

(4) A plurality of voids having a size of 1 nm or less were present between the molecule of the terephthalic acid and the molecule of the n-dodecylamine.

Figure 20:
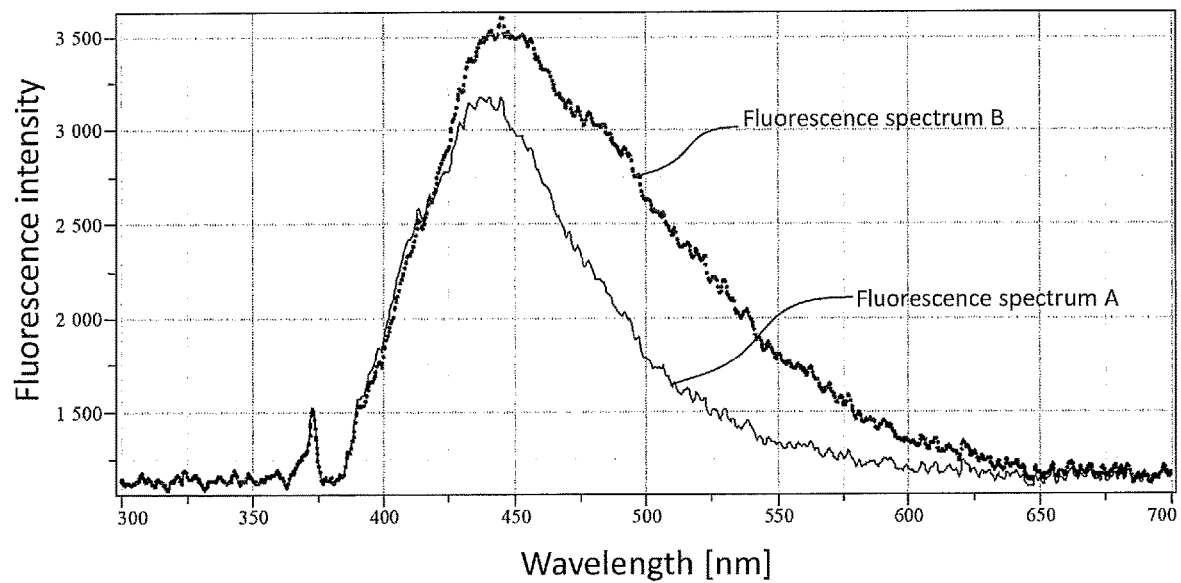
FIG. 20 is a graph showing the fluorescence spectrum A and the fluorescence spectrum B of the terephthalic acid bis(n-dodecylamine) salt produced in Example 4.

The produced terephthalic acid bis(n-dodecylamine) salt was evaluated for ability to detect a hydroxy radical by the same technique as in Example 1. FIG. 20 shows the fluorescence spectrum A and the fluorescence spectrum B of the terephthalic acid bis(n-dodecylamine) salt. As shown in FIG. 20, the fluorescence generated, by the irradiation with the ultraviolet light, from the terephthalic acid bis(n-dodecylamine) salt that had been exposed to the gas containing a hydroxy radical exhibited a higher intensity over a wide wavelength range from 425 nm to 610 nm and a higher intensity at a wavelength of 490 nm than that of the terephthalic acid bis(n-dodecylamine) salt that had not yet been exposed to the gas containing a hydroxy radical. That is, it was confirmed that the terephthalic acid bis(n-dodecylamine) salt had an ability to detect a hydroxy radical.

For comparison, there was measured, in the same manner as the measurement of the fluorescence spectrum A, a fluorescence spectrum of the terephthalic acid bis(n-dodecylamine) salt that had been left, without being exposed to the gas containing a hydroxy radical, for 2 hours in an atmosphere controlled to have a temperature of 21° C. and a relative humidity of 92%. The measured fluorescence spectrum showed no difference from the fluorescence spectrum A.

The produced terephthalic acid bis(n-dodecylamine) salt was evaluated for deliquescency by the same technique as in Example 1. No deliquescency was observed on the terephthalic acid bis(n-dodecylamine) salt that had been left for 2 hours in an atmosphere controlled to have a temperature of 18 to 20° C. and a relative humidity of 100%.

Example 5

The quantity of the obtained mixed solution of the terephthalic acid and the methanol was changed to 200 mL, and 1.52 g (15.05 mmol) of n-hexylamine was used instead of the n-octylamine. 2.17 g (5.88 mmol) of a terephthalic acid (n-hexylamine) salt was obtained in the same manner as in Example 1 except for the above-mentioned conditions.

Figure 21:
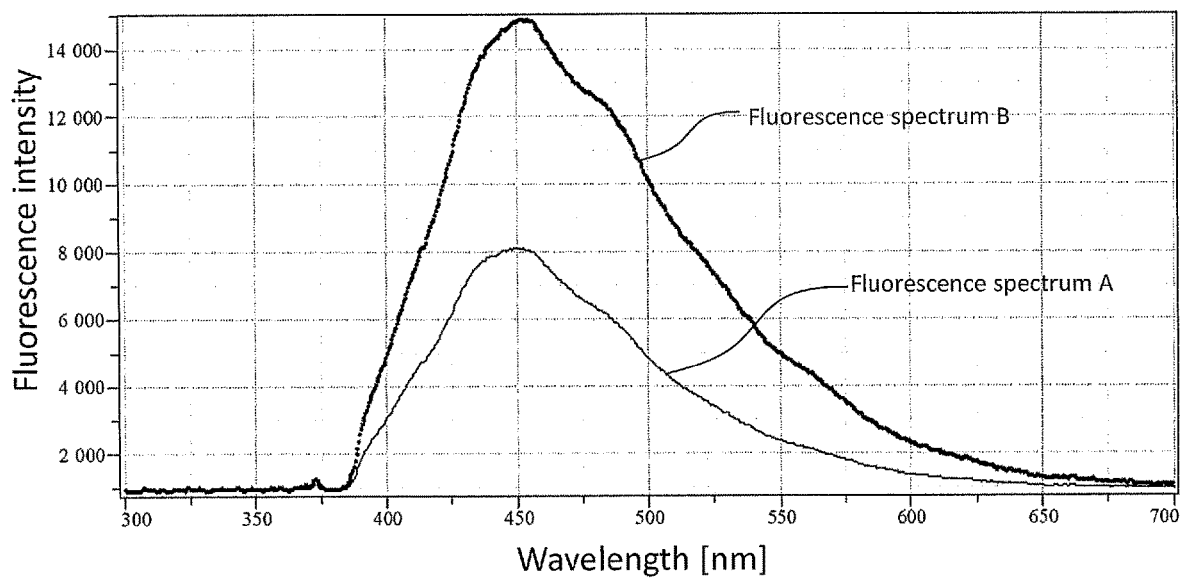
FIG. 21 is a graph showing the fluorescence spectrum A and the fluorescence spectrum B of a terephthalic acid bis(n-hexylamine) salt produced in Example 5.

The produced terephthalic acid bis(n-hexylamine) salt was evaluated for ability to detect a hydroxy radical by the same technique as in Example 1. FIG. 21 shows the fluorescence spectrum A and the fluorescence spectrum B of the terephthalic acid bis(n-hexylamine) salt. As shown in FIG. 21, the fluorescence generated, by the irradiation with the ultraviolet light, from the terephthalic acid bis(n-hexylamine) salt that had been exposed to the gas containing a hydroxy radical exhibited a higher intensity over a wide wavelength range from 385 nm to 650 nm and a higher intensity at a wavelength of 490 nm than the terephthalic acid bis(n-hexylamine) salt that had not yet been exposed to the gas containing a hydroxy radical. That is, it was confirmed that the terephthalic acid bis(n-hexylamine) salt had an ability to detect a hydroxy radical.

For comparison, there was measured, in the same manner as the measurement of the fluorescence spectrum A, a fluorescence spectrum of the terephthalic acid bis(n-hexylamine) salt that had been left, without being exposed to the gas containing a hydroxy radical, for 2 hours in an atmosphere controlled to have a temperature of 21° C. and a relative humidity of 90 to 91%. The measured fluorescence spectrum showed no difference from the fluorescence spectrum A.

The produced terephthalic acid bis(n-hexylamine) salt was evaluated for deliquescency by the same technique as in Example 1. Deliquescency was observed on the terephthalic acid bis(n-hexylamine) salt that had been left for 2 hours in an atmosphere controlled to have a temperature of 18 to 20° C. and a relative humidity of 100%.

Example 6

The quantity of the obtained mixed solution of the terephthalic acid and the methanol was changed to 150 mL, and 1.73 g (15.05 mmol) of n-heptylamine was used instead of the n-octylamine. 2.22 g (5.60 mmol) of a terephthalic acid (n-heptylamine) salt was obtained in the same manner as in Example 1 except for the above-mentioned conditions.

Figure 22:
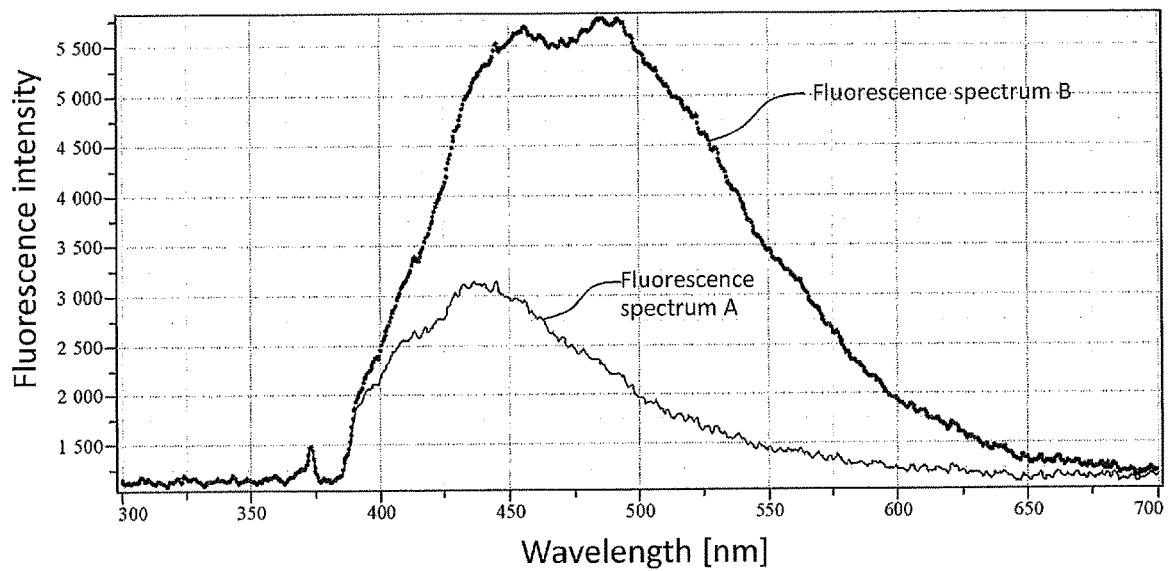
FIG. 22 is a graph showing the fluorescence spectrum A and the fluorescence spectrum B of a terephthalic acid bis(n-heptylamine) salt produced in Example 6.

The produced terephthalic acid bis(n-heptylamine) salt was evaluated for ability to detect a hydroxy radical by the same technique as in Example 1. FIG. 22 shows the fluorescence spectrum A and the fluorescence spectrum B of the terephthalic acid bis(n-heptylamine) salt. As shown in FIG. 22, the fluorescence generated, by the irradiation with the ultraviolet light, from the terephthalic acid bis(n-heptylamine) salt that had been exposed to the gas containing a hydroxy radical exhibited a higher intensity over a wide wavelength range from 385 nm to 650 nm and a higher intensity at a wavelength of 490 nm than that of the terephthalic acid bis(n-hexylamine) salt that had not yet been exposed to the gas containing a hydroxy radical. That is, it was confirmed that the terephthalic acid bis(n-heptylamine) salt had an ability to detect a hydroxy radical.

For comparison, there was measured, in the same manner as the measurement of the fluorescence spectrum A, a fluorescence spectrum of the terephthalic acid bis(n-heptylamine) salt that had been left, without being exposed to the gas containing a hydroxy radical, for 2 hours in an atmosphere controlled to have a temperature of 18 to 23° C. and a relative humidity of 90 to 93%. The measured fluorescence spectrum showed no difference from the fluorescence spectrum A.

The produced terephthalic acid bis(n-heptylamine) salt was evaluated for deliquescency by the same technique as in Example 1. Deliquescency was observed on the terephthalic acid bis(n-heptylamine) salt that had been left for 2 hours in an atmosphere controlled to have a temperature of 18 to 20° C. and a relative humidity of 100%.

Example 7

The quantity of the terephthalic acid was changed to 0.54 g (3.27 mmol), and the quantity of the obtained mixed solution of the terephthalic acid and the methanol was changed to 50 mL. In addition, a mixture of 0.47 g (3.60 mmol) of n-octylamine and 0.52 g (3.60 mmol) of n-nonylamine was used instead of the n-octylamine alone. 1.23 g (2.80 mmol) of a terephthalic acid n-octylamine n-nonylamine mixed salt was obtained in the same manner as in Example 1 except for the above-mentioned conditions.

Figure 23:
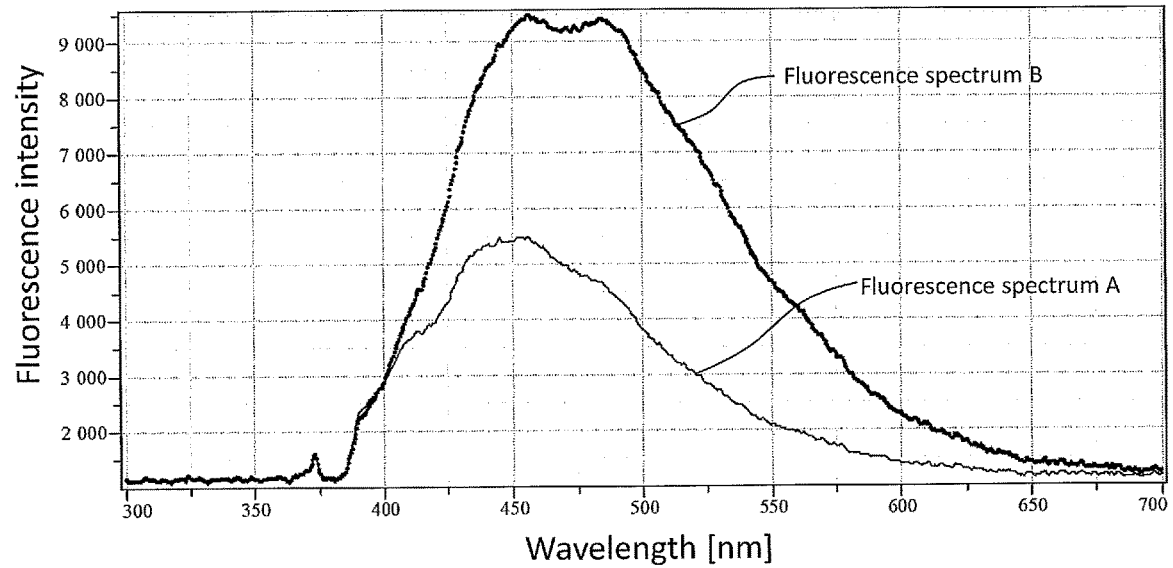
FIG. 23 is a graph showing the fluorescence spectrum A and the fluorescence spectrum B of a terephthalic acid n-octylamine n-nonylamine mixed salt produced in Example 7.

The produced terephthalic acid n-octylamine n-nonylamine mixed salt was evaluated for ability to detect a hydroxy radical by the same technique as in Example 1. FIG. 23 shows the fluorescence spectrum A and the fluorescence spectrum B of the terephthalic acid n-octylamine n-nonylamine mixed salt. As shown in FIG. 23, the fluorescence generated, by the irradiation with the ultraviolet light, from the terephthalic acid n-octylamine n-nonylamine mixed salt that had been exposed to the gas containing a hydroxy radical exhibited a higher intensity over a wide wavelength range from 385 nm to 630 nm and a higher intensity at a wavelength of 490 nm than that of the terephthalic acid n-octylamine n-nonylamine mixed salt that had not yet been exposed to the gas containing a hydroxy radical. That is, it was confirmed that the terephthalic acid n-octylamine n-nonylamine mixed salt had an ability to detect a hydroxy radical.

For comparison, there was measured, in the same manner as the measurement of the fluorescence spectrum A, a fluorescence spectrum of the terephthalic acid n-octylamine·n-nonylamine mixed salt that had been left, without being exposed to the gas containing a hydroxy radical, for 2 hours in an atmosphere controlled to have a temperature of 22° C. and a relative humidity of 93%. The measured fluorescence spectrum showed no difference from the fluorescence spectrum A.

The produced terephthalic acid n-octylamine n-nonylamine mixed salt was evaluated for deliquescency by the same technique as in Example 1. No deliquescency was observed on the terephthalic acid n-octylamine n-nonylamine mixed salt that had been left for 2 hours in an atmosphere controlled to have a temperature of 18 to 20° C. and a relative humidity of 100%.

Comparative Example 1

Figure 24A:
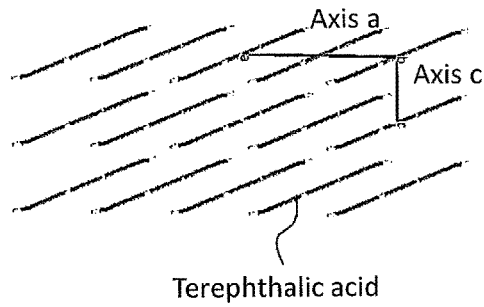
FIG. 24A is a schematic view illustrating a crystal structure of terephthalic acid prepared in Comparative Example 1.
Figure 24B:
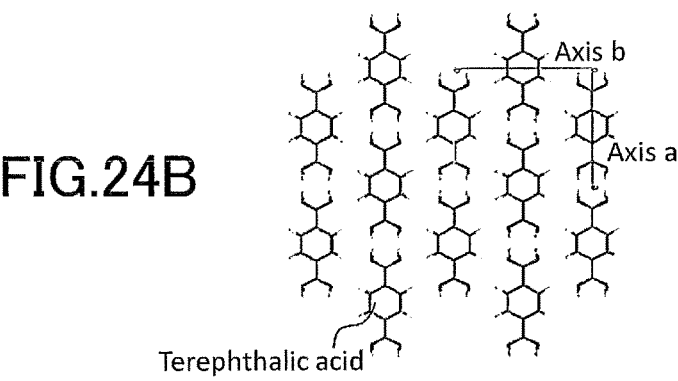
FIG. 24B is a schematic view illustrating the crystal structure of the terephthalic acid prepared in Comparative Example 1.

Terephthalic acid was prepared in Comparative Example 1. A crystal structure of the prepared terephthalic acid was evaluated by the same X-ray crystal structure analysis as in Example 1. FIG. 24A and FIG. 24B show the crystal structure observed by the evaluation. As shown in FIG. 24A and FIG. 24B, it was found that the terephthalic acid had a dense crystal structure based on a n-n stacking interaction. No voids having a size of 1 nm or less were observed between terephthalic acid molecules adjacent to each other.

Figure 25:
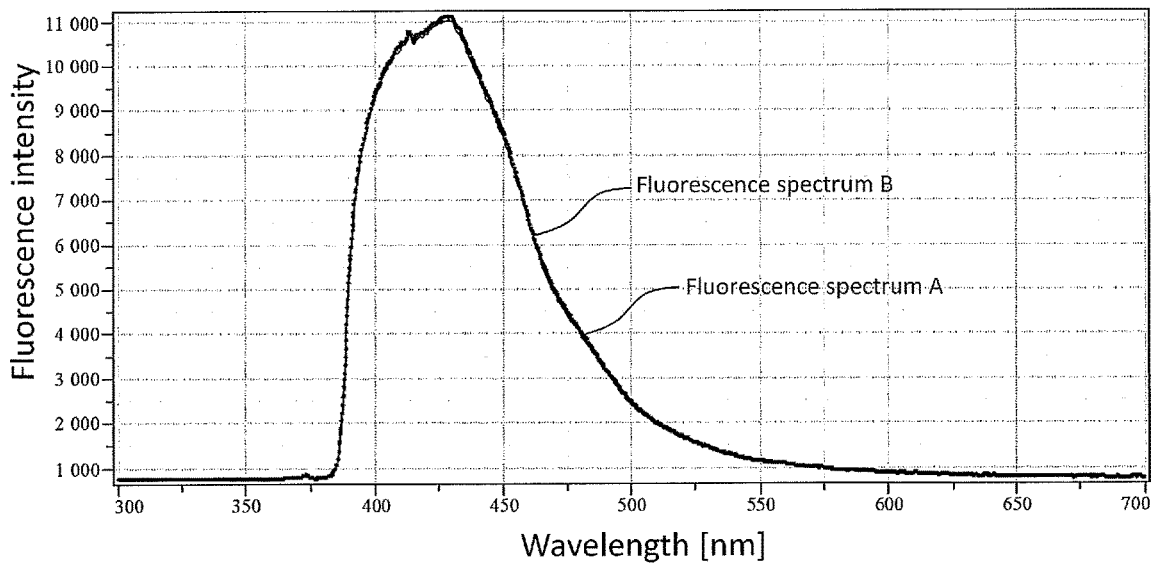
FIG. 25 is a graph showing the fluorescence spectrum A and the fluorescence spectrum B of the terephthalic acid prepared in Comparative Example 1.

The prepared terephthalic acid was evaluated for ability to detect a hydroxy radical by the same technique as in Example 1. FIG. 25 shows the fluorescence spectrum A and the fluorescence spectrum B of the terephthalic acid. As shown in FIG. 25, the exposure to the gas containing a hydroxy radical caused no change in the fluorescence spectrum emitted from the terephthalic acid. That is, it was confirmed that the terephthalic acid in the form of a solid had no ability to detect a hydroxy radical.

Comparative Example 2

The quantity of the obtained mixed solution of the terephthalic acid and the methanol was changed to 200 mL, and 1.17 g (15.07 mmol) of an n-methylamine aqueous solution with a concentration of 40 weight % was used instead of the n-octylamine. 1.36 g (5.96 mmol) of a terephthalic acid bis(n-methylamine) salt was obtained in the same manner as in Example 1 except for the above-mentioned conditions.

Figure 26:
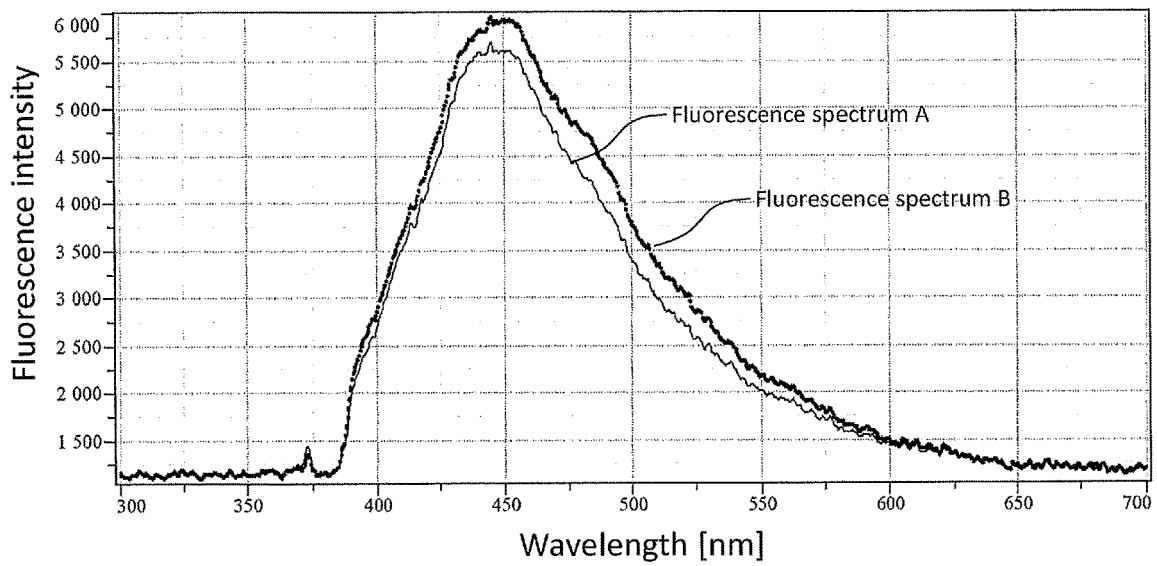
FIG. 26 is a graph showing the fluorescence spectrum A and the fluorescence spectrum B of a terephthalic acid bis(n-methylamine) salt produced in Comparative Example 2.

The prepared terephthalic acid bis(n-methylamine) salt was evaluated for ability to detect a hydroxy radical by the same technique as in Example 1. FIG. 26 shows the fluorescence spectrum A and the fluorescence spectrum B of the terephthalic acid bis(n-methylamine) salt. As shown in FIG. 26, the exposure to the gas containing a hydroxy radical caused almost no change in the fluorescence spectrum emitted from the terephthalic acid bis(n-methylamine) salt. That is, it was confirmed that the terephthalic acid bis(n-methylamine) salt had no ability to detect a hydroxy radical.

For comparison, there was measured, in the same manner as the measurement of the fluorescence spectrum A, a fluorescence spectrum of the terephthalic acid bis(n-methylamine) salt that had been left, without being exposed to the gas containing a hydroxy radical, for 2 hours in an atmosphere controlled to have a temperature of 20° C. and a relative humidity of 93%. The measured fluorescence spectrum showed no difference from the fluorescence spectrum A.

The produced terephthalic acid bis(n-methylamine) salt was evaluated for deliquescency by the same technique as in Example 1. Deliquescency was observed on the terephthalic acid bis(n-methylamine) that had been left for 2 hours in an atmosphere controlled to have a temperature of 18 to 20° C. and a relative humidity of 100%.

Comparative Example 3

The quantity of the obtained mixed solution of the terephthalic acid and the methanol was changed to 200 mL, and 0.97 g (15.05 mmol) of an n-ethylamine aqueous solution with a concentration of 70 weight % was used instead of the n-octylamine. 1.53 g (5.97 mmol) of a terephthalic acid bis(n-ethylamine) salt was obtained in the same manner as in Example 1 except for the above-mentioned conditions.

Figure 27:
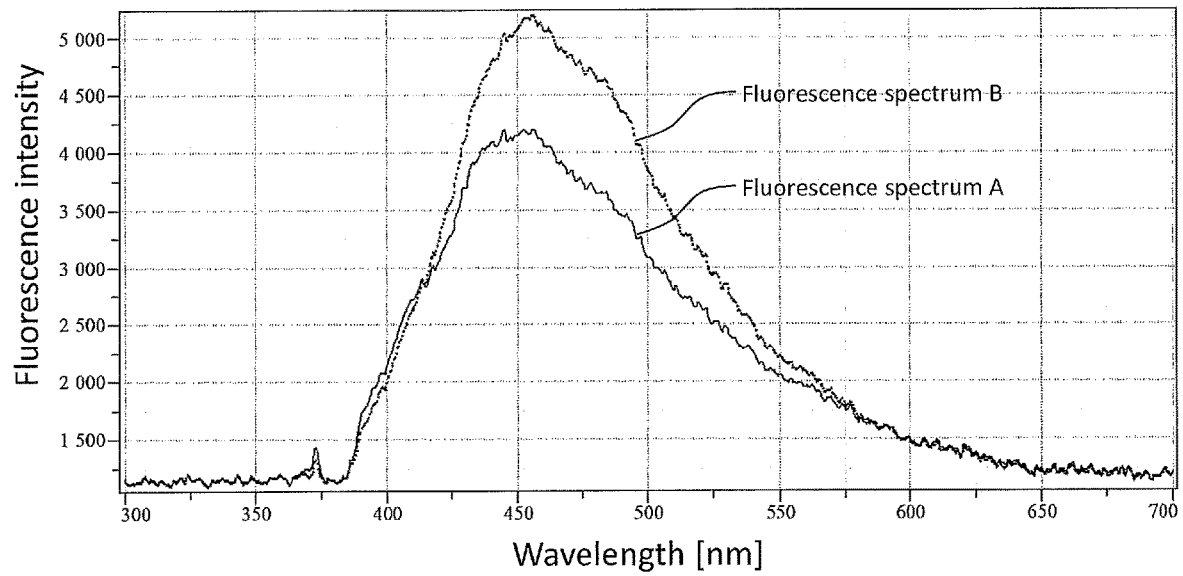
FIG. 27 is a graph showing the fluorescence spectrum A and the fluorescence spectrum B of a terephthalic acid bis(n-ethylamine) salt produced in Comparative Example 3.

The prepared terephthalic acid bis(n-ethylamine) salt was evaluated for ability to detect a hydroxy radical by the same technique as in Example 1. FIG. 27 shows the fluorescence spectrum A and the fluorescence spectrum B of the terephthalic acid bis(n-ethylamine) salt. As shown in FIG. 27, the exposure to the gas containing a hydroxy radical caused almost no change in the fluorescence spectrum emitted from the terephthalic acid bis(n-ethylamine) salt. That is, it was confirmed that the terephthalic acid bis(n-ethylamine) salt had no ability to detect a hydroxy radical.

For comparison, there was measured, in the same manner as the measurement of the fluorescence spectrum A, a fluorescence spectrum of the terephthalic acid bis(n-ethylamine) salt that had been left, without being exposed to the gas containing a hydroxy radical, for 2 hours in an atmosphere controlled to have a temperature of 19° C. and a relative humidity of 92%. The measured fluorescence spectrum showed no difference from the fluorescence spectrum A.

The produced terephthalic acid bis(n-ethylamine) salt was evaluated for deliquescency by the same technique as in Example 1. Deliquescency was observed on the terephthalic acid bis(n-ethylamine) that had been left for 2 hours in an atmosphere controlled to have a temperature of 18 to 20° C. and a relative humidity of 100%.

Comparative Example 4

0.89 g (15.05 mmol) of n-propylamine was used instead of the n-octylamine. 1.68 g (5.91 mmol) of a terephthalic acid bis(n-propylamine) salt was obtained in the same manner as in Example 1 except for the above-mentioned conditions.

Figure 28:
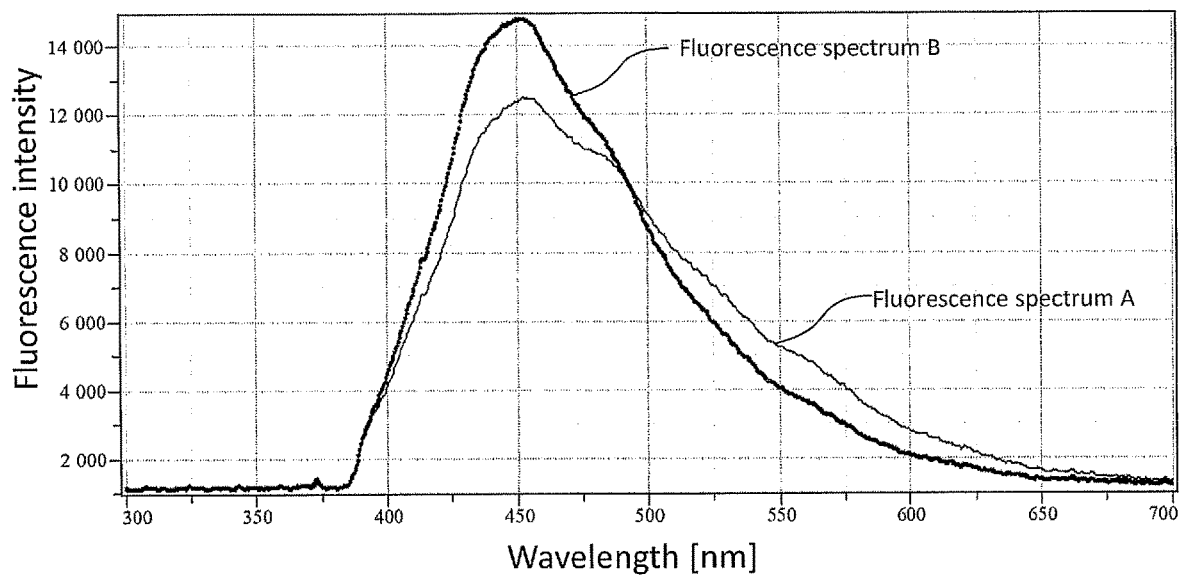
FIG. 28 is a graph showing the fluorescence spectrum A and the fluorescence spectrum B of a terephthalic acid bis(n-propylamine) salt produced in Comparative Example 4.

The prepared terephthalic acid bis(n-propylamine) salt was evaluated for ability to detect a hydroxy radical by the same technique as in Example 1. FIG. 28 shows the fluorescence spectrum A and the fluorescence spectrum B of the terephthalic acid bis(n-propylamine) salt. As shown in FIG. 28, the exposure to the gas containing a hydroxy radical caused almost no change in the fluorescence spectrum emitted from the terephthalic acid bis(n-propylamine) salt. In addition, the fluorescence spectrum was reduced in intensity at a wavelength of 490 nm. That is, it was confirmed that the terephthalic acid bis(n-propylamine) salt had no ability to detect a hydroxy radical.

For comparison, there was measured, in the same manner as the measurement of the fluorescence spectrum A, a fluorescence spectrum of the terephthalic acid bis(n-propylamine) salt that had been left, without being exposed to the gas containing a hydroxy radical, for 2 hours in an atmosphere controlled to have a temperature of 23° C. and a relative humidity of 90 to 92%. The measured fluorescence spectrum showed no difference from the fluorescence spectrum A.

The produced terephthalic acid bis(n-propylamine) salt was evaluated for deliquescency by the same technique as in Example 1. Deliquescency was observed on the terephthalic acid bis(n-propylamine) that had been left for 2 hours in an atmosphere controlled to have a temperature of 18 to 20° C. and a relative humidity of 100%.

Comparative Example 5

The quantity of the obtained mixed solution of the terephthalic acid and the methanol was changed to 200 mL, and 1.95 g (15.05 mmol) of n-butylamine was used instead of the n-octylamine. 2.49 g (5.86 mmol) of a terephthalic acid bis(n-butylamine) salt was obtained in the same manner as in Example 1 except for the above-mentioned conditions.

Figure 29:
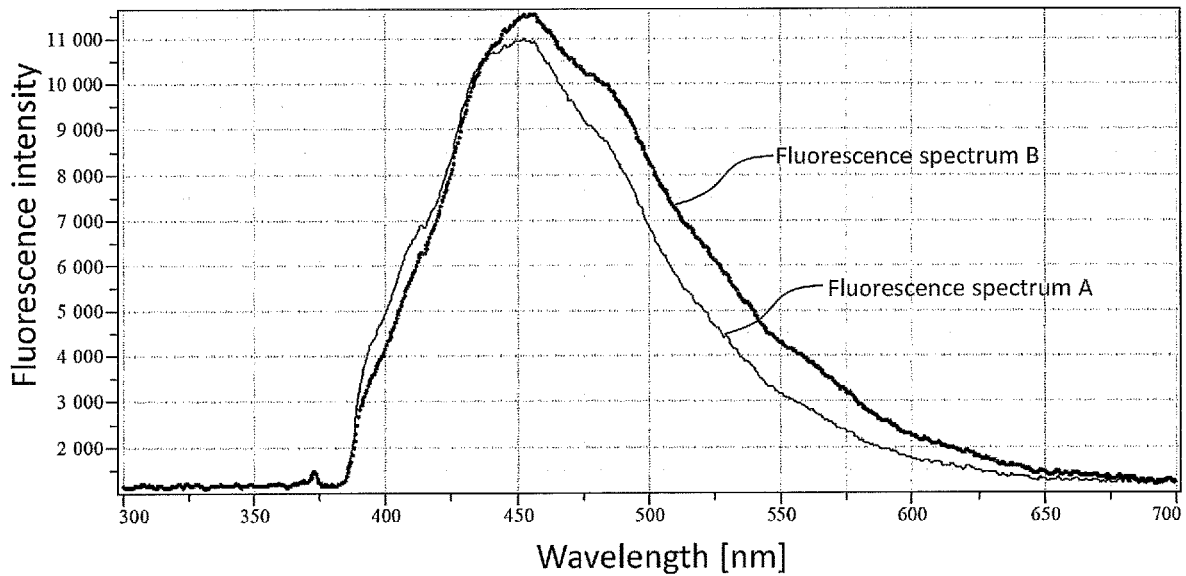
FIG. 29 is a graph showing the fluorescence spectrum A and the fluorescence spectrum B of a terephthalic acid bis(n-butylamine) salt produced in Comparative Example 5.

The prepared terephthalic acid bis(n-butylamine) salt was evaluated for ability to detect a hydroxy radical by the same technique as in Example 1. FIG. 29 shows the fluorescence spectrum A and the fluorescence spectrum B of the terephthalic acid bis(n-butylamine) salt. As shown in FIG. 29, the exposure to the gas containing a hydroxy radical caused almost no change in the fluorescence spectrum emitted from the terephthalic acid bis(n-butylamine) salt. That is, it was confirmed that the terephthalic acid bis(n-butylamine) salt had no ability to detect a hydroxy radical.

For comparison, there was measured, in the same manner as the measurement of the fluorescence spectrum A, a fluorescence spectrum of the terephthalic acid bis(n-butylamine) salt that had been left, without being exposed to the gas containing a hydroxy radical, for 2 hours in an atmosphere controlled to have a temperature of 21° C. and a relative humidity of 91%. The measured fluorescence spectrum showed no difference from the fluorescence spectrum A.

The produced terephthalic acid bis(n-butylamine) salt was evaluated for deliquescency by the same technique as in Example 1. Deliquescency was observed on the terephthalic acid bis(n-butylamine) that had been left for 2 hours in an atmosphere controlled to have a temperature of 18 to 20° C. and a relative humidity of 100%.

Comparative Example 6

The quantity of the terephthalic acid was changed to 2.00 g (12.04 mmol), and the quantity of the obtained mixed solution of the terephthalic acid and the methanol was changed to 500 mL. In addition, 2.52 g (28.89 mmol) of n-pentylamine was used instead of the n-octylamine. 3.72 g (10.93 mmol) of a terephthalic acid bis(n-pentylamine) salt was obtained in the same manner as in Example 1 except for the above-mentioned conditions.

Figure 30:
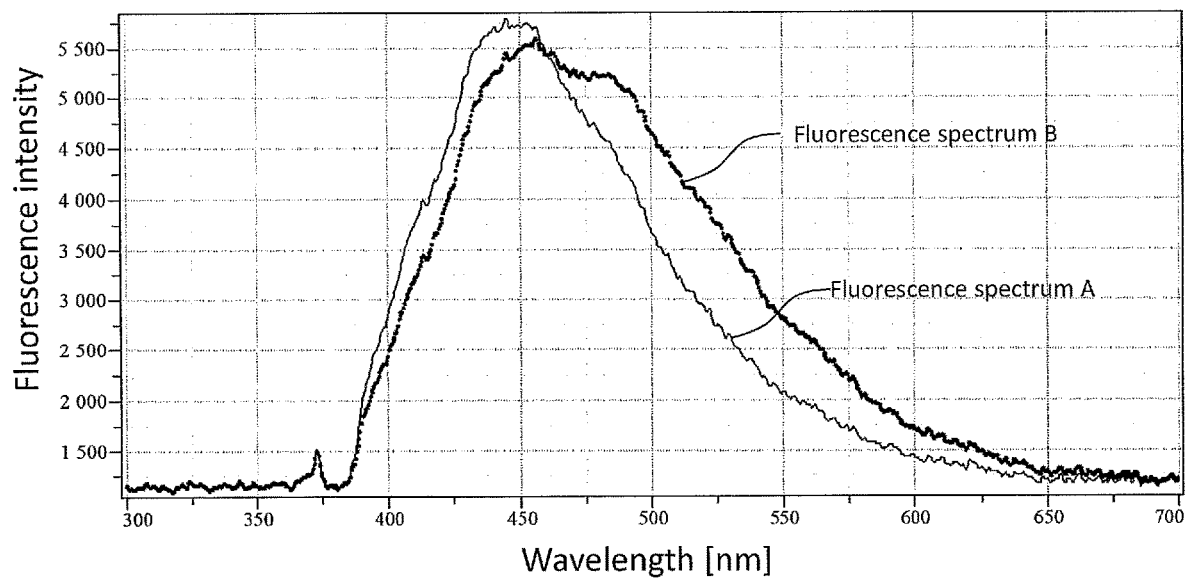
FIG. 30 is a graph showing the fluorescence spectrum A and the fluorescence spectrum B of a terephthalic acid bis(n-pentylamine) salt produced in Comparative Example 6.

The prepared terephthalic acid bis(n-pentylamine) salt was evaluated for ability to detect a hydroxy radical by the same technique as in Example 1. FIG. 30 shows the fluorescence spectrum A and the fluorescence spectrum B of the terephthalic acid bis(n-pentylamine) salt. As shown in FIG. 30, the exposure to the gas containing a hydroxy radical caused almost no change in the fluorescence spectrum emitted from the terephthalic acid bis(n-pentylamine) salt. That is, it was confirmed that the terephthalic acid bis(n-pentylamine) salt had no ability to detect a hydroxy radical.

For comparison, there was measured, in the same manner as the measurement of the fluorescence spectrum A, a fluorescence spectrum of the terephthalic acid bis(n-pentylamine) salt that had been left, without being exposed to the gas containing a hydroxy radical, for 2 hours in an atmosphere controlled to have a temperature of 21° C. and a relative humidity of 91 to 93%. The measured fluorescence spectrum showed no difference from the fluorescence spectrum A.

The produced terephthalic acid bis(n-pentylamine) salt was evaluated for deliquescency by the same technique as in Example 1. Deliquescency was observed on the terephthalic acid bis(n-pentylamine) that had been left for 2 hours in an atmosphere controlled to have a temperature of 18 to 20° C. and a relative humidity of 100%.

Comparative Example 7

The quantity of the terephthalic acid was changed to 0.50 g (3.01 mmol), and 1.78 g (6.62 mmol) of n-octadecylamine was used instead of the n-octylamine. 1.82 g (2.59 mmol) of a terephthalic acid bis(n-octadecylamine) salt was obtained in the same manner as in Example 1 except for the above-mentioned conditions.

Figure 31:
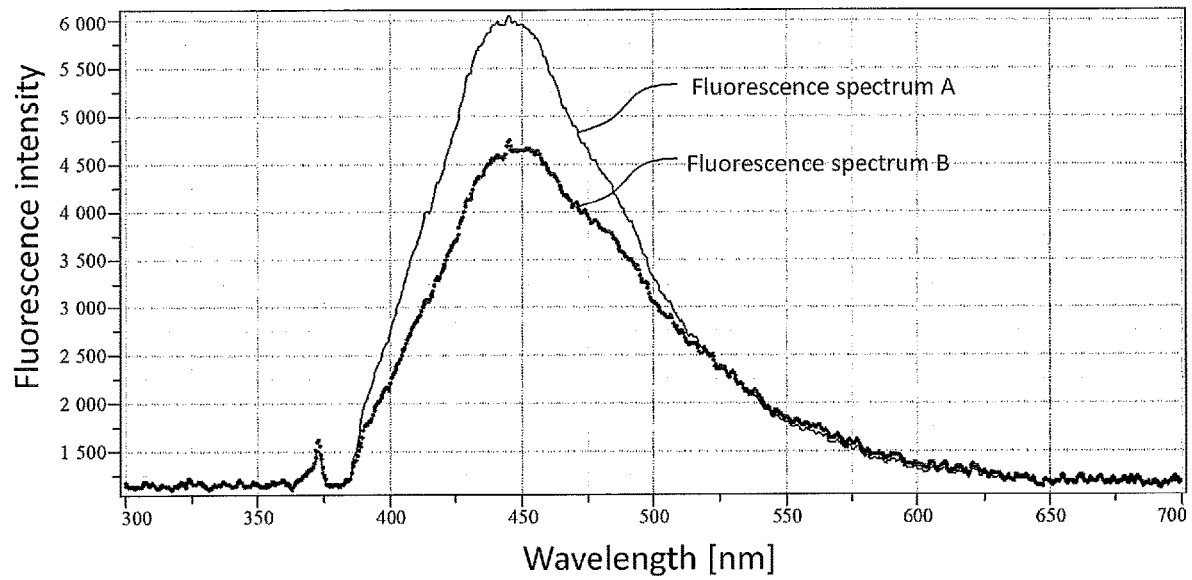
FIG. 31 is a graph showing the fluorescence spectrum A and the fluorescence spectrum B of a terephthalic acid bis(n-octadecylamine) salt produced in Comparative Example 7.

The prepared terephthalic acid bis(n-octadecylamine) salt was evaluated for ability to detect a hydroxy radical by the same technique as in Example 1. FIG. 31 shows the fluorescence spectrum A and the fluorescence spectrum B of the terephthalic acid bis(n-octadecylamine) salt. As shown in FIG. 31, the exposure to the gas containing a hydroxy radical reduced the intensity of the fluorescence spectrum emitted from the terephthalic acid bis(n-octadecylamine) salt. That is, it was confirmed that the terephthalic acid bis(n-octadecylamine) salt had no ability to detect a hydroxy radical.

For comparison, there was measured, in the same manner as the measurement of the fluorescence spectrum A, a fluorescence spectrum of the terephthalic acid bis(n-octadecylamine) salt that had been left, without being exposed to the gas containing a hydroxy radical, for 2 hours in an atmosphere controlled to have a temperature of 22° C. and a relative humidity of 91%. The measured fluorescence spectrum showed no difference from the fluorescence spectrum A.

The produced terephthalic acid bis(n-octadecylamine) salt was evaluated for deliquescency by the same technique as in Example 1. No deliquescency was observed on the terephthalic acid bis(n-octadecylamine) that had been left for 2 hours in an atmosphere controlled to have a temperature of 18 to 20° C. and a relative humidity of 100%.

Figure 32:
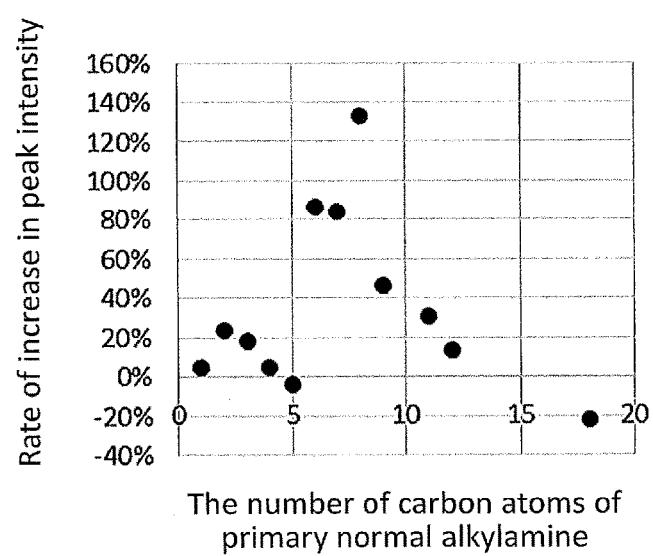
FIG. 32 is a graph showing a relationship between the number of carbon atoms of an alkyl group constituting the primary alkylamine contained in each of the organic salts produced in Examples 1 to 6 and Comparative Examples 2 to 7 and the rate of increase in peak intensity.
Figure 33:
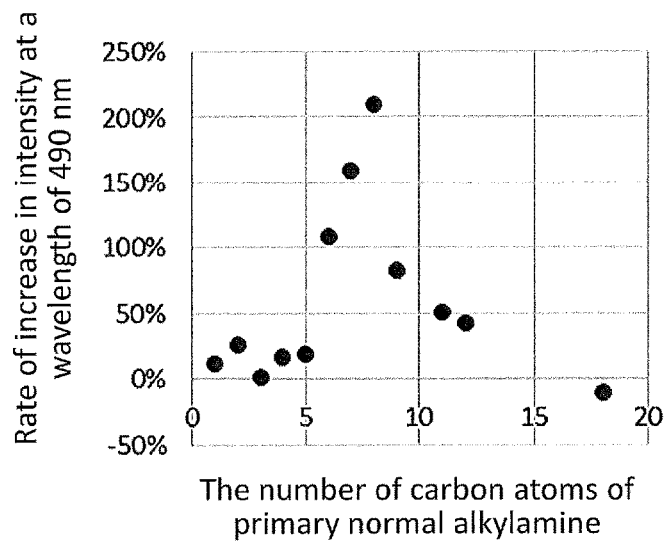
FIG. 33 is a graph showing a relationship between the number of carbon atoms of the alkyl group constituting the primary alkylamine contained in each of the organic salts produced in Examples 1 to 6 and Comparative Examples 2 to 7 and the rate of increase in intensity of the fluorescence spectra of these organic salts at a wave length of 490 nm.

Table 1 collectively shows the peak wavelength, the peak intensity, and the intensity at a wavelength of 490 nm of the fluorescence spectrum A emitted from each of the organic salts produced in Examples 1 to 6 and Comparative Examples 2 to 7 that had not yet been exposed to the gas containing a hydroxy radical as well as the peak wavelength, the peak intensity, and the intensity at a wavelength of 490 nm of the fluorescence spectrum B emitted from each of the organic salts produced in Examples 1 to 6 and Comparative Examples 2 to 7 that had been exposed to the gas containing a hydroxy radical. In addition, Table 1 shows the rate of increase in peak intensity and the rate of increase in intensity at a wavelength of 490 nm before and after the exposure to the gas containing a hydroxy radical as well as deliquescency evaluation results. Furthermore, FIG. 32 shows a relationship between the number of carbon atoms of an alkyl group constituting the primary alkylamine and the rate of increase in peak intensity. Also, FIG. 33 shows a relationship between the number of carbon atoms of the alkyl group constituting the primary alkylamine and the rate of increase in intensity at a wave length of 490 nm. As shown in FIG. 32 and FIG. 33, the ability to detect a hydroxy radical was exhibited when the alkyl group constituting the primary alkylamine has 6 or more and 17 or less carbon atoms. Moreover, as shown in Table 1, the deliquescency was inhibited when the alkyl group constituting the primary alkylamine has 8 or more carbon atoms.

TABLE 1

| | | Before exposure | | | After exposure | | | | | |
|---|---|---|---|---|---|---|---|---|---|---|
| | Primary alkylamine | Peak wavelength (nm) | Peak intensity (a. u.) | Intensity at a wavelength of 490 nm (a. u.) | Peak wavelength (nm) | Peak Intensity (a. u.) | Rate of increase in peak intensity (%) | Intensity at a wavelength of 490 nm (a. u.) | Rate of increase in intensity at a wavelength of 490 nm (%) | Deliquescency |
| Comparative Example 2 | n-methylamine | 445 | 5693 | 3933 | 445 | 5964 | 4.8 | 4385 | 11.5 | Observed |
| Comparative Example 3 | n-ethylamine | 456 | 4198 | 3455 | 456 | 5201 | 23.9 | 4365 | 26.4 | Observed |
| Comparative Example 4 | n-propylamine | 453 | 12489 | 10314 | 452 | 14811 | 18.6 | 10432 | 1.1 | Observed |
| Comparative Example 5 | n-butylamine | 452 | 11001 | 8108 | 456 | 11548 | 5 | 9473 | 16.8 | Observed |
| Comparative Example 6 | n-pentylamine | 445 | 5797 | 4258 | 456 | 5596 | −3.5 | 5072 | 19.1 | Observed |
| Example 5 | n-hexylamine | 450 | 8102 | 5716 | 452 | 15114 | 86.5 | 11916 | 108.5 | Observed |
| Example 6 | n-heptylamine | 445 | 3128 | 2207 | 486 | 5768 | 84.4 | 5711 | 158.7 | Observed |
| Example 1 | n-octylamine | 445 | 2456 | 1820 | 485 | 5711 | 132.5 | 5644 | 210.1 | Not observed |
| Example 2 | n-nonylamine | 445 | 2383 | 1870 | 484 | 3487 | 46.4 | 3419 | 82.9 | Not observed |
| Example 3 | n-undecylamine | 445 | 1936 | 1565 | 445 | 2533 | 30.9 | 2352 | 50.3 | Not observed |
| Example 4 | n-dodecylamine | 437 | 3179 | 2032 | 445 | 3605 | 13.4 | 2889 | 42.2 | Not observed |
| Comparative Example 7 | n-octadecylamine | 445 | 6056 | 3945 | 445 | 4745 | −21.7 | 3525 | −10.6 | Not observed |

Example 8

Experiment 2 of Exposure to Body Surface Gas

The detection medium 33 having the structure shown in FIG. 5 was prepared. The body part 34A and the cover 34B were made of polytetrafluoroethylene. As the organic salt 1, a pellet of the terephthalic acid bis(n-octylamine) salt produced in Example 1 was used. The pellet was produced by filling an aluminum open-type specimen container (GAA-0068 available from Hitachi High-Tech Science Corporation) with 5 mg of the terephthalic acid bis(n-octylamine) salt and then pressing it with a pressing machine.

Next, the prepared detection medium 33 was attached to a belt imitating a band of a wrist watch and left for 2 hours while being in contact with a surface of a wrist of a person serving as a test subject. The detection medium 33 was attached to the belt in such a manner that an opening of the through hole 36 was in contact with the wrist of the person.

Figure 34:
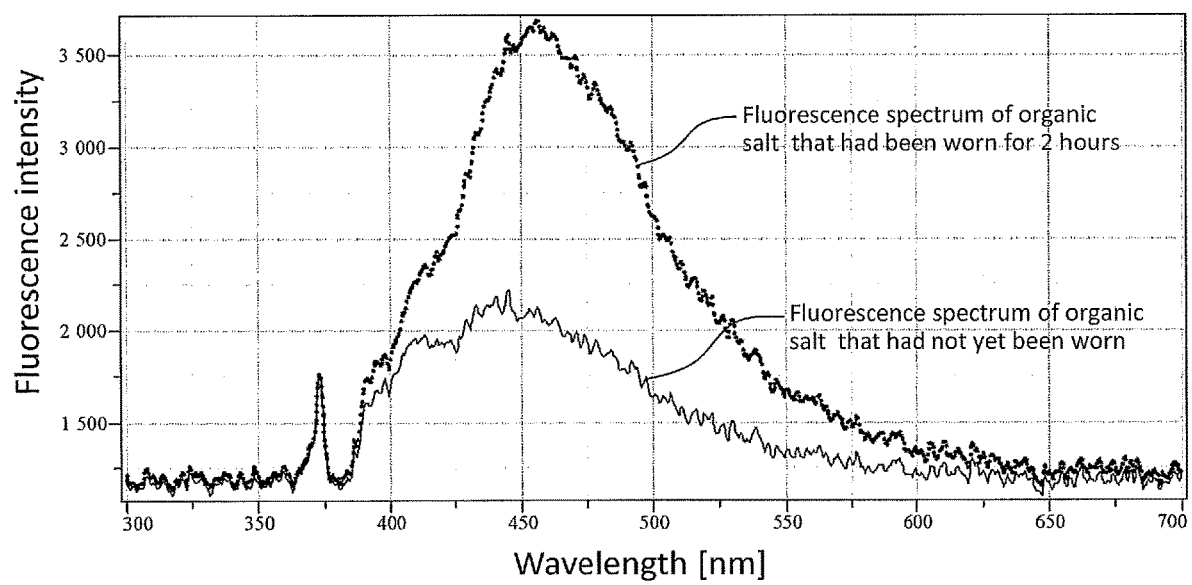
FIG. 34 is a graph showing a change between the fluorescence spectrum of the organic salt before exposure to a body surface gas and the fluorescence spectrum of the organic salt after exposure to the body surface gas when a detection medium produced in Example 8 is used.

A fluorescence spectrum of the organic salt 1 that had not yet been left and a fluorescence spectrum of the organic salt 1 that had been left were measured as in Example 1. FIG. 34 shows the measurement results of the fluorescence spectra. As shown in FIG. 34, the fluorescence generated, by the irradiation with the ultraviolet light, from the organic salt 1 that had been exposed to the body surface gas exhibited a higher intensity over a wide wavelength range from 385 nm to 620 nm and a higher intensity at a wavelength of 490 nm than that of the organic salt 1 that had not yet been left. That is, it was confirmed that a hydroxy radical contained in the body surface gas can be detected using the detection medium 33.

INDUSTRIAL APPLICABILITY

An organic salt of the present disclosure can be used to detect a hydroxy radical contained in a gas, for example. The organic salt of the present disclosure is applicable, for example, to a hydroxy-radical sensor configured to detect a hydroxy radical contained in a gas.

The invention claimed is:

1. An organic salt comprising terephthalic acid and at least one kind primary alkylamine, wherein
an alkyl group constituting the primary alkylamine has 6 or more and 9 or less carbon atoms.

2. The organic salt according to claim 1, wherein the alkyl group is a normal alkyl group.

3. The organic salt according to claim 1, wherein the alkyl group has 8 or more carbon atoms.

4. The organic salt according to claim 1, wherein the organic salt has a supramolecular crystal structure including a molecule of the primary alkylamine and a molecule of the terephthalic acid.

5. The organic salt according to claim 4, wherein the supramolecular crystal structure has a void between the molecule of the primary alkylamine and the molecule of the terephthalic acid.

6. The organic salt according to claim 1, wherein the organic salt is for detecting a hydroxy radical contained in a gas.

7. A hydroxy-radical sensor configured to detect a hydroxy radical contained in a gas, comprising:
an exposure unit that includes an organic salt and has a structure in which the organic salt can be in contact with the gas;
a light source configured to irradiate the organic salt of the exposure unit with ultraviolet light; and
a light detector configured to detect fluorescence generated from the organic salt by the irradiation with the ultraviolet light, wherein
the hydroxy-radical sensor detects the hydroxy radical contained in the gas based on the fluorescence detected by the light detector,
the organic salt comprises terephthalic acid and at least one primary alkylamine, and an alkyl group constituting the primary alkylamine has 6 or more and 17 or less carbon atoms.

8. The hydroxy-radical sensor according to claim 7, wherein the exposure unit is detachable as a detection medium.

9. A detection medium configured to be used for detecting a hydroxy radical contained in a gas,
   comprising the organic salt according to claim 1 and
   having a structure configured so that the organic salt can be in contact with the gas and allow for detection of a hydroxy radical contained in the gas.

10. A method comprising:
   exposing an organic salt to a gas to be tested for presence of hydroxy radical, the organic salt including terephthalic acid and at least one primary alkylamine;
   irradiating the organic salt with light from a light source;
   detecting with a light detector fluorescence generated from the organic salt by the irradiating of the organic salt; and
   determining the presence of hydroxy radical in the tested gas based on the detected fluorescence,
   wherein an alkyl group constituting the primary alkylamine has 6 or more and 17 or less carbon atoms.

* * * * *